US006448235B1

(12) United States Patent
Linden et al.

(10) Patent No.: US 6,448,235 B1
(45) Date of Patent: *Sep. 10, 2002

(54) METHOD FOR TREATING RESTENOSIS WITH A2A ADENOSINE RECEPTOR AGONISTS

(75) Inventors: Joel M. Linden; Gail W. Sullivan; Ian Sarembock, all of Charlottesville; W. Michael Sheld, Earlysville, all of VA (US)

(73) Assignee: University of Virginia Patent Foundation, Charlottesville, VA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/543,385

(22) Filed: Apr. 4, 2000

Related U.S. Application Data

(63) Continuation of application No. 09/003,930, filed on Jan. 8, 1998, now abandoned, which is a continuation-in-part of application No. 08/272,821, filed on Jul. 11, 1994, now Pat. No. 5,877,180.

(51) Int. Cl.[7] ............................................. A61K 31/70
(52) U.S. Cl. ......................................................... 514/46
(58) Field of Search ............................................ 514/46

(56) References Cited

U.S. PATENT DOCUMENTS

| | | | |
|---|---|---|---|
| 3,892,777 A | 7/1975 | Greunman et al. | 260/340.5 |
| 4,193,926 A | 3/1980 | Schmiechen et al. | 260/326.5 |
| 4,242,345 A | 12/1980 | Brenner et al. | 424/253 |
| 4,665,074 A | 5/1987 | Amschler | 514/247 |
| 4,824,660 A | 4/1989 | Angello et al. | 424/1.1 |
| 4,879,296 A | 11/1989 | Daluge et al. | 514/263 |
| 4,938,949 A | 7/1990 | Borch et al. | 424/10 |
| 4,956,345 A | 9/1990 | Miyasaka et al. | 514/46 |
| 4,965,271 A | 10/1990 | Mandell et al. | 514/263 |
| 5,070,877 A | 12/1991 | Mohiuddin et al. | 128/653.4 |
| 5,096,906 A | 3/1992 | Mandell et al. | 514/263 |
| 5,124,455 A | 6/1992 | Lombardo et al. | 546/181 |
| 5,140,015 A | 8/1992 | Olsson et al. | 514/46 |
| 5,189,027 A | 2/1993 | Miyashita et al. | 514/46 |
| 5,272,153 A | 12/1993 | Mandell et al. | 514/263 |
| 5,278,150 A | 1/1994 | Olsson et al. | 514/46 |
| 5,298,508 A | 3/1994 | Jacobson et al. | 514/263 |
| 5,565,462 A | 10/1996 | Eitan et al. | 514/262 |
| 5,593,975 A | 1/1997 | Cristalli | 514/46 |
| 5,665,754 A | 9/1997 | Feldman et al. | 514/397 |
| 5,668,139 A | 9/1997 | Belardinelli et al. | 514/263 |
| 5,696,254 A | 12/1997 | Mansour et al. | 536/27.11 |
| 5,731,296 A | 3/1998 | Sollevi | 536/46 |
| 5,756,706 A | 5/1998 | Mansour et al. | 536/27.11 |
| 5,854,081 A | 12/1998 | Linden et al. | 436/501 |
| 5,877,180 A | 3/1999 | Linden et al. | 514/266 |
| 5,932,558 A | 8/1999 | Cronstein et al. | 514/46 |
| 5,998,386 A | 12/1999 | Feldman | 514/46 |
| 6,004,945 A | 12/1999 | Fukunaga | 514/46 |
| RE36,494 E | 1/2000 | Olsson et al. | 514/46 |
| 6,020,321 A | 2/2000 | Cronstein et al. | 514/46 |
| 6,020,339 A | 2/2000 | Perrier et al. | 514/269 |
| 6,034,089 A | 3/2000 | Han et al. | 514/269 |
| 6,339,072 B2 | 1/2002 | P.L. et al. | 514/46 |

FOREIGN PATENT DOCUMENTS

| | | |
|---|---|---|
| EP | 0700908 | 3/1996 |
| WO | 95/11681 | 5/1995 |
| WO | 96/04280 | 2/1996 |
| WO | 98/47509 | 10/1998 |
| WO | 98/57651 | 12/1998 |
| WO | 99/63938 | 12/1999 |
| WO | 00/44763 | 1/2000 |

OTHER PUBLICATIONS

Sullivan, G.W., et al., "Neutrophil A2A Adenosine Receptor Inhibits Inflammation in a Rat Model of Meningitis: Synergy with the Type IV Phosphodiesterase Inhibitor, Rolipram", *The Journal of Infectious Disease*, 180, No. 5, pp. 1550–1560, (1999).

Baraldi, P.G., et al., "Synthesis and Biological Activity of a New Series of N6–Arylcarbamoyl, 2–(Ar)alrkynyl–6–Oarylcarbamoyl, and N6–Carboxamido derivatives of adenosine–5'–N–ethyluronamide as A1 and A3 Adenosine receptor agonist", *J. Med. Chem.*, vol. 41, No. 17, XP002149470, 3174–3185, (1998).

Mager, P.P., "Neutal network approaches applied to selective A2a adenosine receptor agonists", *Med. Chem. Res.*, vol. 8, No. 6, XP000952528, 277–290, (1998).

Okusa, M.D., et al., "Selective A2A adenosine receptor activation reduces ischemia–reperfusion injury in rat kidney", *Am. J. Physiol.*, 3 (Pt 2), XP000952524, pp. F404–F412, (1999).

Ali, H., et al., "Methylxanthines Block Antigen–induceed Responses in RBL–2H3 Cells Independently of Adenosine Receptors or Cyclic AMP: Evidence for Inhibition of Antigen Binding to IgE", *Journal of Pharmacology and Experimental Therapeutics*, 258, pp. 954–962, (1991).

Andersson, P., et al., "Anti–anaphylactic and anti–inflammatory effects of xanthines in the lung", *Curr. Clin. Pract. Ser.*, pp. 187–192, (1985).

Berkich, D.A., et al., "Evidence of Regulated Coupling of $A_1$ Adenosine Receptors by Phosphorylation in Zucker Rats.", *American Journal of Physiology*, 268 (4), pp. E693–E704, (Apr. 1995).

(List continued on next page.)

Primary Examiner—William R. A. Jarvis
(74) Attorney, Agent, or Firm—Schwegman, Lundberg, Woessner & Kluth, P.A.

(57) ABSTRACT

Agonists of $A_{2A}$ adenosine receptors in combination with rolipram, its derivatives or other Type IV phosphodiesterase (PDE) inhibitors are effective for the treatment of restenosis.

10 Claims, 9 Drawing Sheets

OTHER PUBLICATIONS

Bhattacharya, S., et al., "Effects of Long–term Treatment With the Allosteric Enhancer, PD81,723, on Chinese Hamster Ovary Cells Expressing Recombitant Human $A_1$ Adenosine Receptors", *Molecular Pharmacology, 50 (1)*, pp. 104–111, (Jul. 1996).

Bhattacharya, S., et al., "The Allosteric Enhancer, PD 81,723, Stabilizes Human $A_1$ Adenosine Receptor Coupling to G Proteins", *Biochimica et Biophysica Acta, 1265 (1)*, pp. 15–21, (Feb. 1995).

Bridges, A.J., et al., "$N^6$–[2–(3,5–Dimethoxyphenyl)–2–(2–Methylphenyl)–Ethyl]Adenosine and Its Uronamide Derivatives. Novel Adenosine Agonists With Both High Affinity and High Selectivity for the Adenosine $A_2$ Receptor", *Journal of Medicinal Chemistry, 31(7)*, pp. 1282–1285, (1988).

Bruns, R.F., "Adenosine Receptors—Roles and Pharmacology", *Biological Actions of Extracellular ATP, 603*, Annals of The New York Academy of Sciences, pp. 211–226, (1990).

Bruns, R.F., et al., "Characterization of the $A_2$ Adenosine Receptor Labeled by [$^3$H]NECA in Rat Striatal Membranes", *Molecular Pharmacology, 29*, pp. 331–346, (1986).

Buster, B., et al., "The Effect of Adenosine Receptor Agonists on Neutrophil Pleocytosis and Blood–Brain Barrier Pathophysiology in Experimental Bacterial Meningitis", *Abstract of the Interscience Conference on Antimicrobial Agents and Chemotherapy, 37*, Abstract No. B–72, p. 39, (1997).

Carruthers, A.M., et al., "Hypotensive Responses to the Putative Adenosine $A_3$ Receptor Agonist $N^6$–20(4–Aminophenyl)–Ethyladenosine in the Rat", *Drug Development Research, 30*, pp. 147–152, (1993).

Cembrzynska, N.M., et al., "Elevated Release of Tumor Necrosis Factor–alpha and Interferon–gamma by Bronchoalveolar Leukocytes From Patients With Bronchial Asthma.", *American Review of Respiratory Disease, 147(2)*, 291–295, (1993).

Cothran, D.L., et al., "Ontogeny of Rat Myocardial $A_1$ Adenosine Receptors", *Biol Neonate, 68 (2)*, pp. 111–118, (1995).

Cristalli, G., et al., "Alkynyl Derivatives of Adenosine an Adenosine–5'–N–ethyluranamide as Selective Agonists at $A_2$ Adenosine Receptors1", *Journal of Medicinal Chemistry, 35(13)*, 2363–2368, (1992).

Cronstein, B.N., et al., "Adenosine Modulates the Generation of Superoxide Anion by Stimulated Human Neutrophils Via Interaction With a Specific Cell Surface Receptor", *Annals New York Academy of Science, 451*, 291–314, (1985).

Cronstein, B.N., et al., "Adenosine; A Physiologic Modulator Of Superoxide Anion Generated By Human Neutrophils. Adenosine Acts Via An $A_2$ Receptor On Human Neutrophils", *Journal Of Immunology, 135(2)*, 1366–1371, (1985).

Cronstein, B.N., et al., "Engagement of Adenosine Receptors Inhibits Hydrogen Peroxide ($H_2O_2$) Release by Activated Human Neutrophils", *Clinical Immunology and Immunopathology, 42(1)*, 76–85, (1987).

Cronstein, B.N., et al., "Methotrexate Inhibits Leukocyte Influx Into Inflammatory Sites Via The Adenosine ($A_2$) Receptor", *Clinical Research, 41(2)*, 244A, (1993).

Cronstein, B.N., et al., "The Adenosine/Neutrophil Paradox Resolved: Human Neutrophils Possess Both $A_1$ and $A_2$ Receptors That Promote Chemotaxis and Inhibits $O_2$ Generation, Respectively", *Journal of Clinical Investigation, 85(4)*, 1150–1157, (1990).

Cronstein, N., et al., "Occupancy Of Adenosine Receptors Raises Cyclic AMP Alone And In Synergy With Occupancy Of Chemoattractant Receptors And Inhibits Membrane Depolarization", *Biochemical Journal, 252(3)*, 709–715, (1988).

De La Harpe, J., et al., "Adenosine Regulates the Respiratory Burst Of Cytokine –Triggered Human Neutrophils Adherent To Biological Surfaces", *Journal Of Immunology, 143(2)*, 596–602, (1989).

de Moraes, V.L., et al., "Effect of Cyclo–Oxygenase Inhibitors and Modulators of Cyclic AMP Formation on Lipopolysaccharide–Induced Neutrophil Infiltration in Mouse Lung", *British Journal of Pharmacology, 117*, pp. 1792–1796, (1996).

Dinarello, C.A., "Interleukin–1 And Tumor Necrosis Factor: Effector Cytokines In Autoimmune Disease", *Seminars in Immunology, 4*, 133–145, (1992).

Doyle, M.P., et al., "Nucleoside–induced Arteriolar Constriction: a Mast Cell–dependent Response.", *American Journal of Physiology*, pp. H2042–H2050, (May 1994).

Fang, G.D., et al., "A New Selective Adenosine $A_{2a}$ Receptor Agonist, Improves Survival in *E. coli* O26:B6 Lipopolysaccharide (LPS)–Induced Experimental Murine Endotoxemia", *Journal of Investigative Medicine*, Abstract No. 797, p. 148A, (2000).

Feoktistov, I., et al., "Adenosine $A_{2b}$ receptors", *The American Society for Pharmacological and Experimental Therapeutics, 49 (4)*, pp. 381–402, (1997).

Feoktistov, I., et al., "Role of Adenosine in Asthma", *Drug Development Research, 39*, pp. 333–336, (1996).

Ferrante, A., et al., "Optimal Conditions for Simultaneous Purification of Mononuclear and Polymorphonuclear Leucocytes From Human Blood by the Hypaque–Ficoll Method", *Journal of Immunological Methods, 36(2)*, 109, (1980).

Figler, R.A., et al., "Reconstitution of Bovine $A_1$ Adenosine Receptors and G Proteins in Phospholipid Vesicles: βγ–Subunit Composition Influences Guanine Nucleotide Exchange and Agonist Binding", *Biochemistry, 36 (51)*, pp. 16288–16299, (1997).

Figler, R.A., et al., "Reconstitution of Recombinant Bovine $A_1$ Adenosine Receptors in Sf9 Cell Membrane with Recombinant G Proteins of Defined Composition.", *Molecular Pharmacology, 50 (6)*, pp. 1587–1595, (Dec. 1996).

Firestein, G.S., et al., "Adenosine Regulating Agents: A Novel Approach to Inflammation and Inflammatory Arthritis", *Clinical Rsearch, 41(2)*, 170A, (1993).

Fozard, J.R., "Adenosine $A_3$ Receptors Mediate Hypotension in the Angiotensin II–supported Circulation of the Pithed Rat", *British Journal of Pharmacology, 109 (1)*, pp. 3–5, (1993).

Francis, J.E., et al., "Highly Selective Adenosine $A_2$ Receptor Agonists in a Series of N–Alkylated 2–Aminoadenosines", *Journal of Medicinal Chemistry, 34 (8)*, pp. 2570–2579, (1991).

Gao, Z., et al., "$A_{2B}$ Adenosine and $P2Y_2$ Receptors Stimulate Mitogen–activated Protein Kinase in Human Embryonic Kidney–293 Cells. Cross–talk Between Cyclic AMP and Protein Kinase c Pathways", *The Journal of Biological Chemistry, 274* (*9*), pp. 5972–5980, (Feb. 26, 1999).

Gao, Z., et al., "Purification of $A_1$ Adenosine Receptor–G–protein Complexes: Effects of Receptor Down–regulation and Phosphorylation on Coupling", *Biochemical Journal, 338* (*Pt3*), pp. 729–736, (Mar. 1999).

Gilchrist, A., et al., "Antagonists of the Receptor–G Protein Interface Block Gi–coupled Signal Transduction", *The Journal of Biological Chemistry, 273* (*24*), pp. 14912–14919, (Jun. 12, 1998).

Glover, D.K., et al., "Pharmacological Stress Thallium Scintigraphy With 2–Cyclohexylmethylidenehydrazinoadenosine (WRC–0470) A Novel, Short–Acting Adenosine $A_{2A}$ Receptor Agonist.", *Circulation, 94*, pp. 1726–1732, (1996).

Griswold, D.E., et al., "Effects of Selective Phosphodiesterase Type IV Inhibitor, Rolipram, on Fluid and Cellular Phases of Inflammatory Response", *Chemical Abstracts, 119*, Abstract No. 173828e, p. 49, (1993).

Hanlon, W.A., et al., "rTNF alpha Facilitate Human Polymorphonuclear Leukocyte Adherence to Fibrinogen Matrices With Mobilization of Specific and Tertiary But Not Azurophilic Granule Markers", *Journal of Leukocyte Biology, 50* (*1*), pp. 43–48, (1991).

Hartung, H.P., "Immune–Mediated Demyelination", *Annals of Neurology, 33* (*6*), pp. 563–567, (Jun. 1993).

Heller, L.J., et al., "Effect of Adenosine on Histamine Release and Artrioventricular Conduction During Guinea Pig Cardia Anaphylaxis", *Circulation Research, 62* (*6*), pp. 1147–1158, (Jun. 1988).

Holmes, et al., "Restenosis After Percutaneous Transluminal Coronary Angioplasty (PTCA): A Report From the PTCA Registry of the National Heart, Lung, and Blood Institute", *American Journal of Cardiology, 53*, 77C–81C, (1984).

Hussain, T., et al., "$^{125}$1–APE Binding to Adenosine Receptors in Coronary Artery: Photoaffinity Labelling With $^{125}$1–adizoAPE", *The Journal of Pharmacology and Experimental Therapeutics, 276* (*1*), pp. 284–288, (Jan. 1996).

Hutchinson, A.J., et al., "2–(Arylakylamino)Adenosine–5'–Uronamides: A New Class of Highly Selective Adenosine $A_2$ Receptor Ligands", *Journal of Medicinal Chemistry, 33* (*7*), pp. 1919–1924, (1990).

Hutchinson, A.J., et al., "CGS 21680C, and $A_2$ Selective Adenosine Receptor Agonist With Preferential Hypotensive Activity", *The Journal of Pharmacology and Experimental Therapeutics, 251* (*1*), pp. 47–55, (1989).

Iannone, M.A., et al., "Effects of Adenosine on Human Neutrophil Function and Cyclic AMP Content", *Topics and Perspectives in Adenosine Research*, eds. E. Gerlach et al., Springer–Verlag, Berlin, Proceedings of the 3rd International Symposium on Adenosine, Munich, Jun. 1986, 286–298, (1986).

Imagawa, D.K., et al., "The Role of Tumor Necrosis Factor in Allograft Rejection", *Transplantation, 51*, 57–62, (Jan. 1991).

Ito, B.R., et al., "Role of Cardiac Mast Cells In Complement C5a–induced Myocardial Ischemia", *American Journal of Physiology, 264* (*5*), Part 2 ot Two Parts, pp. H1346–H1354, (May 1993).

Jarvis, M.F., et al., "[$^3$H]CGS 21680, A Selective $A_2$ Adenosine Receptor Agonist Directly Labels $A_2$ Receptors in Rat Brain.", *Journal of Pharmacology and Experimental Therapeutics, 251*(*3*), 888–893, (Aug. 1989).

Jolly, S.R., et al., "Effects of Lodoxarnide on Ischemica Reperfused Myocardium", *Journal of Cardiovascular Pharmacology, 4* (*3*), pp. 441–448, (1982).

Kaminuma, et al., "Effect of T–440, a Novel Type IV Phosphodiesterase Inhibitor, on Allergen–Induced Immediate and Late Asthmatic Reaction and Leukocyte Infiltration into the Airways of Guinea Pigs", *International Archives of Allergy & Immunology, 112*(*4*), 406–411, (1997).

Keller, A.M., et al., "Acute Reoxygeneration Injury in the Isolated Rat Heart: Role of Resident Cardiac Mast Cells", *Circulation Research, 63* (*6*), pp. 1044–1052, (Dec. 1988).

Kennedy, A.P., et al., "Covalent Modification of Transmembrane Span III of the $A_1$ Adenosine Receptor With an antagonist Photoaffinity Probe.", *Molecular Pharmacology, 50*, pp. 789–798, (Oct. 1996).

Kollias–Baker, C., et al., "Allosteric Enhancer PD 81,723 Acts by Novel Mechanism to Potentiate Cardiac Actions of Adenosine", *Circulation Research, 75* (*6*), pp. 961–971, (Dec. 1994).

Koshiba, M., et al., "Patterns of $A_{2A}$ Extracellular Adenosine Receptor Expression in Different Functional Subsets of Human Peripheral T Cells. Flow Cytometry Studies With Anti–$A_{2A}$ Receptors Monoclonal Antibodies.", *Molecular Pharmacology, 55* (*3*), pp. 614–624, (Mar. 1999).

Leclerc, G., et al., "Percutaneous Arterial Gene Transfer in a Rabbit Model", *Journal of Clinical Investigation, 90* (*3*), pp. 936–944, (1992).

Legrand–Poels, S., et al., "Activation of Human Immunodeficiency Virus Type 1 by Oxidative Stress", *AIDS Research and Human Retroviruses, 6*(*12*), 1389–1397, (1990).

Lette, J., et al., "Safety of Dipyridamole Testing in 73,806 Patients: The Multicenter Dipyridamole Safety Study", *Journal of Nuclear Cardiology, 2* (*1*), pp. 3–17, (1995).

Linden, J., "Allosteric Enhancement of Adenosine Receptors", *In: Purinergic Approaches in Experimental Therapeutics, Chapter 5*, Edited by K.A. Jacobson et al., and Published by Wiley–Liss, Inc., pp. 85–97, (1997).

Linden, J., "Cloned Adenosine $A_3$ Receptors: Pharmacological Properties, Species Differences and Receptor Functions.", *Trends in Pharmacological Sciences, 15* (*8*), pp. 298–306, (Aug. 1994).

Linden, J., "Recombinant Techniques as Applied to the Study of $A_1$ Adenosine Receptors", *In: Adenosine and Adenine Nucleotides: From Molecular Biolgy to Integrative Physiology, Chapter 2*, Kluwer Academic Publishers, Boston, Edited by L. Belardinelli, pp. 15–19, (1995).

Linden, J., et al., "($^{125}$I)Aminobenzyladenosine, a New Radioligand with Improved Specific Binding to Adenosine Receptos in Heart", *Circulation Research, 56* (*2*), pp. 279–284, (Feb. 1985).

Linden, J., et al., "Adenosine Receptors", *In: Handbook of Receptors and Channels—G Protein Coupled Receptors, Chapter 2*, Edited by S.J. Peroutka, Published by CRC Press, Boca Raton, FL, pp. 29–44, (1994).

Linden, J., et al., "Molecular Cloning and Functional Expression of a Sheep $A_3$ Adenosine Receptor with Widespread Tissue Distribution", *Molecular Pharmacology, 44* (*3*), pp. 524–532, (Sep. 1993).

Linden, J., et al., "The Structure and Function of $A_1$ and $A_{2B}$ Adenosine Receptors", *Life Sceince, 62 (17/18)*, pp. 1519–1524, (1998).

Luthin, D.R., et al., "Adenosine Receptors", *Biomembranes, 2B*, pp. 321–347, (1996).

Luthin, D.R., et al., "Characterization of Two Affinity States of Adenosine $A_{2a}$ Receptors with a New Radioligand, 2–[2–(4–amino–3–[$^{125}$1]iodophenyl) Ethylamino]Adenosine.", *Molecular Pharmacology, 47(2)*, pp. 307–313, (Feb. 1995).

Luthin, D.R., et al., "Comparison of $A_4$ and $A_{2a}$ Binding Sites in Striatum and COS Cells Transfected With Adesosine $A_{2a}$ Receptors.", *The Journal of Pharmacology and Experimental Therapeutics, 272*, pp. 511–518, (Feb. 1995).

Luthin, D.R., et al., "Photoaffinity Labeling With 2–[2–(4–azido–3–[$^{125}$1]–iodophenyl)ethylamino]Adenosine and Autoradiography With 2–[2–(4–amino–3–[$^{125}$1]iodophenyl)ethylamino]Adenosine of $A_{2a}$ Adenosine Receptor in Rat Brain.", *Journal of Neurochemistry, 65 (5)*, pp. 2072–2079, (Nov. 1995).

Mahan, L.C., et al., "Cloning and Expression of an $A_1$ Adenosine Receptor from Rat Brain", *Molecular Pharmacology, 40 (1)*, pp. 1–7, (Jul. 1991).

Mannel, D.N., et al., "Tumor Necrosis Factor: A Cytokine Involved in Toxic Effects of Endotoxin", *Reviews of Infectious Diseases, 9*, S602–S606, (1987).

Martin, P.L., et al., "Characterization of 8–(N–methylisopropyl)amino–N$^6$–(5'–endohydroxy–endonorbornyl)–9–methyladenine (WRC–0571), a Highly Potent and Selective, Non–xanthine Antagonist of $A_1$ Adenosine Receptors.", *The Journal of Pharmacology and Experimental Therapeutics, 276 (2)*, pp. 490–499, (Feb. 1996).

Martin, P.L., et al., "Pharmacology of 2–cyclohexylmethylidenehydrazinoadenosine (WRC–0470), a Novel, Short–acting Adenosine $A_{2A}$ Receptor Agonist That Produces Selective Coronary Vasodilation.", *Drug Development Research, 40 (4)*, pp. 313–324, (1997).

Matherne, G.P., et al., "Transgenic $A_1$ Adenosine Receptor Overexpression Increases Myocardial Resistance to Ischemia", *Proceedings of the National Academy of Science, 94*, pp. 6541–6546, (Jun. 1997).

Matsuyama, T., et al., "Cytokines and HIV Infection: is AIDS a Tumor Necrosis Factor Disease?", *AIDS, 5(12)*, 1405–1417, (1991).

McGarrity, S.T., et al., "Inhibition of Neutrophil Superoxide Anion Generation by Platelet Products: Role of Adenine Nucleotides", *Journal of Leukocyte Biology, 44(5)*, 411–421, (1988).

McGarrity, S.T., et al., "Regulation of Human Neutrophil Function by Adenine Nucleotides", *Journal of Immunology, 142(6)*, 1986–1994, (1989).

McLaughlin, D.P., et al., "Hemodynamic and Metabolic Correlates of Dipyridamole–induced Myocardial Thallium–201 Perfusion Abnormalities in Multivessel Coronary Artery Disease.", *American Journal of Cardiology, 73 (16)*, pp. 1159–1164, (Jun. 1994).

Merritt, H.R., et al., "Abnormal Q Waves are Common Early in AMI and Do Not Predict Decreased Myocardial Salvage With Thrombolytic Therapy", *Special Issue Journal of American College of Cardiology*, Abstract No. 895–77, p. 195A, (Feb. 1994).

Mizumura, T., et al., "PD 81,723, an Allosteric Enhancer of the $A_1$ Adenosine Receptor, Lowers the Threshold for Ischemic Preconditioning in Dogs.", *Circulation Research, 79 (3)*, pp. 415–423, (Sep. 1996).

Molnar–Kimber, K.L., et al., "Modulation of TNFα and IL–1β From Endotoxin–Stimulated Monocytes by Selective PDE Isozyme Inhibitors", *Agents & Actions, 39*, C77–C79, (1993).

Mumby, S.M., et al., "G–protein alpha–subunit expression, myristoylation, and membrane association in COS cells", *Proceedings of the National Academy of Sciences, 87 (2)*, pp. 728–732, (Jan. 1990).

Nabel, E.G., et al., "Site–Specific Gene Expression in Vivo by Direct Gene Transfer into the Arterial Wall", *Science, 249*, 1285–1288, (1990).

Newman, K.D., et al., "Adenovirus–mediated Gene Transfer into Normal Rabbit Arteries Results in Prolonged Vascular Cell Activation, Inflammation and Neointimal Hyperplasia", *Journal of Clinical Investigation, 96(6)*, 2955–2965, (1995).

Nielson, C.P., et al., "Effects of Adenosine on Polymorphonuclaer Leucocyte Function, Cyclic 3': 5'–adenosine Monophosphate, and Intracellular Calcium", *British Journal of Pharmacology, 97(3)*, 882–888, (1989).

Niiya, K., et al., "2–(N'–Aklylidenehydrazino)Adenosines: Potent and Selective Coronary Vasodilators", *Journal of Medicinal Chemistry, 35(24)*, 4557–4561, (1992).

Nolte, "Reduction of Postischemic Leukocyte–Endothelium Interaction by Adenosine Via $A_2$ Receptor", *Biological Abstract, 94 (11)*, Abstract No. 116779, 1 p., (1992).

O'Regan, M.H., et al., "Adenosine Receptor Agonists Inhibit the Release of γ–Aminobutyric Acid (GABA) From the Ischemic Rat Cerebral Cortex", *Chemical Abstracts, 117*, Abstract No. 104867p, p. 170, (1992).

Olsson, R.A., et al., "N$^6$–Substituted N–Alkyladenosine–5'–Uronamides: Bifunctional Ligands Having Recognition Groups for A1 and A2 Adenosine Receptors", *Journal of Medicinal Chemistry, 29 (9)*, pp. 1683–1689, (1986).

Peet, N.P., et al., "Conformationally Restrained Chiral (Phenylisopropyl)Amino–Substituted Pyrazolo[3,4–d]Pyrimidines and Purines With Selectivity for Adenosine $A_1$ and $A_2$ Receptors", *Journal of Medicinal Chemistry, 35 (17)*, pp. 3263–3269, (1992).

Pfister, J.R., et al., "Synthesis and Biological Evaluation of the Enantiomers of the Potent and Selective $A_1$– adenosine Antagonist 1,3–dipropyl–8–[2–(5,6–epoxynorbonyl)]–xanthine", *Journal of Medicinal Chemistry, 40 (12)*, pp. 1773–1778, (Jun. 1997).

Ranhosky, A., et al., "The Safety of Intravenous Dipyridamole Thallium Mycardial Perfusion Imaging", *Circulation, 81(4)*, pp. 1205–1209, (Apr. 1990).

Roberts, P.A., et al., "Inhibition of Adenosine of Reactive Oxygen Metabolite Production by Human Polymorphonuclear Leucocytes", *Biochemical Journal, 227(2)*, 669–674, (1985).

Robeva, A.S., et al., "Double Tagging Recombinant $A_1$– and $A_{2A}$–Adenosine Receptors With Hexahistidine and the FLAG Epitope. Development of an Efficient Generic Protein Purification Procedure.", *Biochemical Pharmacology, 51(4)*, pp. 545–555, (Feb. 1996).

Robeva, A.S., et al., "Molecular Characterization of Recombinant Human Adenosine Receptors", *Drug Development Research, 39*, pp. 243–252, (1996).

Rosin, D.L., et al., "Immunohistochemical Localization of Adenosine $A_{2A}$ Receptors in the Rat Central Nervous System", *The Journal of Comparative Neurology*, pp. 163–186, (1998).

Rothe, G.A., et al., "Flow Cytometric Measurement of the Respiratory Burst Activity of Phagocytes Using Dihydrorhodamine 123", *Journal of Immunological Methods, 138(1)*, 133–135, (1991).

Sawmiller, D.R., et al., "Effects of Xanthine Amine Congener on Hypoxic Resistence and Venous and Epicardial Adenosine Concentrations.", *Cardiovascular Research, 28 (5)*, pp. 604–609, (May 1994).

Schiffmann, S.N., et al., "Distribution of adenosine $A_2$ receptor mRNA in the human brain", *Neuroscience Letters, 130*, pp. 177–181, (1991).

Schlack, et al., "Adenosine $A_2$–Receptor Activation at Reperfusion reduces Infarct Size and Improves Myocardial Wall Function in Dog Heart", *Biological Abstract, 96 (6)*, Abstract No. 67801, 1 p., (1993).

Schrier, D.J., et al., "Effects of Adenosine Agonsists on Human Neutrophil Function", *Journal of Immunology, 137(10)*, 3284–3289, (1986).

Seekamp, A., et al., "Ischemia—Reperfusion Injury", *Agents and Actions Supplements, 41*, 137–152, (1993).

Sharief, M.K., et al., "Elevated Serum Levels of Tumor Necrosis Factor–α in Guillain–Barre Syndrome", *Annals of Neurology, 33*, 591–596, (Jun. 1993).

Shepherd, R.K., et al., "Adenosine–induced Vascoconstriction in Vivo. Role of the Mast Cell and $A_3$ Adenosine Receptor.", *Circulation Research, 78 (4)*, pp. 627–634, (Apr. 1996).

Sipka, S., et al., "Adenosine Induced Delay of Expression of AIDS Virus, HIV, in H9T Cells", *Acta. Biochimica et Biophysica Hungarica, 23(1)*, 75–82, (1988).

Siragy, H.M., et al., "Sodium Intake Markedly Alters Renal Interstitial Fluid Adenosine", *Hypertension, 27 (3 Pt 1)*, pp. 404–407, (Mar. 1996).

Smits, P., et al., "Cardiovascular effects of two xanthines and the relation to adenosine antagonism", *Clinical Pharmacology and Therapeutics, 45 (6)*, pp. 593–599, (1989).

Sullivan, G.W., et al., "Adenosine (ADO) Modulates Endotoxin and TNF–Induced PMN Activation", *Clinical Research, 41(2)*, 172A, (1993).

Sullivan, G.W., et al., "Role of $A_{2A}$ Adenosine Receptors in Inflammation", *Drug Development Research, 45 (3/4)*, pp. 103–112, (1998).

Sullivan, G.W., et al., "The Specific Type IV Phosphodiesterase Inhibitor Rolipram Combined with Adenosine Reduces Tumor Necrosis Factor–α–Primed Neutrophil Oxidative Activity", *International Journal of Immunopharmacology, 17(10)*, 793–803, (1995).

Sullivan, G.W., et al., "Two Methylanthines, Pentoxifylline (PTX) and Caffeine (CAF) Have Divergent Effects on Tumor Necrosis Factor (TNF)–Primed Human Neutrophil (PMN) Activation", *Clinical Research, 41(2)*, p. 172A, (1993).

Topol, E.J., et al., "Randomised Trial of Coronary Intervention With Antibody Against Platelet IIb/IIIa integrin for Reduction of Clinical Restenosis: Results at Six Months", *The Lencet, 343(8902)*, 881–886, (1994).

Tracey, K.J., et al., "Cachetin/Tumor Necrosis Factor Induces Cachexia, Anemia, and Inflammation", *Journal of Experimental Medicine, 167*, 1211–1227, (Mar. 1988).

Tucker, A.L., et al., "$A_1$ Adenosine Receptors. Two Amino Acids are Responsible for Species Differences in Ligand Recognition", *Journal of Biological Chemistry, 269 (45)*, pp. 27900–27906, (Nov. 1994).

Ueeda, M., et al., "2– Alkoxyadenosines: Potent and Selective Agonists at the Coronary Artery $A_2$ Adenosine Receptor", *Journal of Medicinal Chemistry, 34(4)*, 1334–1339, (1991).

Ukena, D., et al., "Species Differences in Structure–Activity Relationships of Adenosine Agonists and Xanthine Antagonists at Brain $A_1$ Adenosine Receptors", *FEBS Letters, 209 (1)*, pp. 122–128, (Dec. 1986).

Underwood, D.C., et al., "Inhibition of Antigen–Induced Bronchoconstriction and Eosinophil Infiltration in the Guinea by the Cyclic AMP–Specific Phosphodiesterase Inhibitor, Rolipram", *Chemical Abstracts, 119 (16)*, Abstract No. 173975a, p. 67, (1993).

van Calker, D., et al., "Adenosine Regulates via Two Different Types of Receotors, the Accumulation of Cyclic AMP in Cultured Brain Cells", *Journal of Neurochemistry, 33*, pp. 999–1005, (1979).

Van Calker, D., et al., "Carbamazepine Distinguishes Between Adenosine Receptors That Mediate Different Second Messenger Responses", *European Journal of Pharmacology, 206(4)*, 285–290, (1991).

Walker, B.A., et al., "Adenosine $A_{2a}$ Receptor Activation Delays Apoptosis in Human Neutrophils", *The American Association of Immunologists*, pp. 2926–2931, (1997).

Wan, A.A., et al., "Binding of the Adenosine $A_2$ Receptor Ligand ($^3$H) CGS 21680 to Human and Rat Brain: Evidence for Multiple Affinity Sites", *Journal of Neurochemistry*, pp. 1763–1771, (1990).

Wolff, A.A., et al., "Ventricular Arrhythmias Parallel Cardiac Histamine Efflux After Coronary Artery Occlusion in the Dog", *Agents and Actions, 25 (3/4)*, pp. 296–306, (1988).

Yoneyama, F., et al., "Vasodepressor Mechanisms of 2–(1–octynl) –Adenosine (TY–146), a Selective Adenosine $A_2$ Receptor Agonist, Involve the Opening of Glibenclamide–sensitive $K^+$ Channels", *European Journal of Pharmacology, 213 (1)*, pp. 199–204, (1992).

Takguchi, Y., et al., "Early administration of YT–146, an adenosine A2 receptor agonist, inhibits neointimal thickening after rat femoral artery endothelium injury", *European Journal of Pharmacology 281 (1995) 205–207*, 205–207, (Mar. 16, 1995).

METHOD FOR TREATING RESTENOSIS WITH A2A ADENOSINE RECEPTOR AGONISTS

RELATED APPLICATION

This application is a continuation of U.S. patent application Ser. No. 09/003,930, filed Jan. 8, 1998, now abandoned, which is a continuation-in part of U.S. patent application Ser. No. 08/272,821, filed Jul. 11, 1994 to Linden et al., now U.S. Pat. No. 5,877,180 which is incorporated herein in its entirety by reference.

The present invention was made with the assistance of U.S. Government funding (NIH Grant R01-HL 37942). The U.S. Government may have some rights in this invention.

BACKGROUND OF THE INVENTION

1. Field of the Invention

The present invention relates to methods and compositions for treating inflammatory diseases.

2. Discussion of the Background

The release of inflammatory cytokines such as tumor necrosis factor-alpha (TNFα) by leukocytes is a means by which the immune system combats pathogenic invasions, including infections. Cytokines stimulate neutrophils to enhance oxidative (e.g., superoxide and secondary products) and nonoxidative (e.g., myeloperoxidase and other enzymes) inflammatory activity. Inappropriate and over-release of cytokines can produce counterproductive exaggerated pathogenic effects through the release of tissue damaging oxidative and nonoxidative products (Tracey, K. G., et al., *J. Exp. Med.*, vol. 167, pp. 1211–1227 (1988); and Mannel, D. N., et al., *Rev. Infect. Dis.*, vol. 9 (suppl 5), pp. S602–S606 (1987)).

For example, inflammatory cytokines have been shown to be pathogenic in: arthritis (Dinarello, C. A., *Semin. Immunol.*, vol. 4, pp. 133–45 (1992)); ischemia (Seekamp, A., et al.,*Agents-Actions-Supp.*, vol. 41, pp. 137–52 (1993)); septic shock (Männel, D. N., et al., *Rev. Infect. Dis.*, vol. 9, (suppl 5), pp. S602–S606 (1987)); asthma (Cembrzynska Nowak M., et al.,*Am. Rev. Respir. Dis.*, vol. 147, pp. 291–5 (1993)); organ transplant rejection (Imagawa, D. K., et al., *Transplantation*, vol. 51, pp. 57–62 (1991)); multiple sclerosis (Hartung, H. P., *Ann. Neurol.*, vol. 33, pp. 591–6 (1993)); and AIDS (Matsuyama, T., et al., *AIDS*, vol. 5, pp. 1405–1417 (1991)). In addition, superoxide formation in leukocytes has been implicated in promoting replication of the human immunodeficiency virus (HIV) (Legrand-Poels, S., et al., *AIDS Res. Hum. Retroviruses*, vol. 6, pp. 1389–1397 (1990)).

It is well known that adenosine and some relatively nonspecific analogs of adenosine decrease neutrophil production of inflammatory oxidative products (Cronstein, B. N., et al.,*Ann. N.Y. Acad. Sci.*, vol. 451, pp. 291–314 (1985); Roberts, P. A., et al., *Biochem. J.*, vol. 227, pp. 66.9–674 (19–85); Schrier, D. J., et al., *J. Immunol.*, vol. 137, pp. 3284–3289 (1986); Cronstein, B. N., et al., *Clinical Immunol. and Immunopath.*, vol. 42, pp. 76–85 (1987); Iannone, M. A., et al., in *Topics and Perspectives in Adenosine Research*, E. Gerlach et al., eds., Springer-Verlag, Berlin, pp. 286–298 (1987); McGarrity, S. T., et al., *J. Leukocyte Biol.*, vol. 44, pp. 411421 (1988); De La Harpe, J., et al., *J. Immunol.*, vol. 143, pp. 596–602 (1989); McGarrity, S. T., et al., *J. Immunol.*, vol. 142, pp. 1986–1994 (1989); and Nielson, C. P., et al.,*Br. J. Pharmacol.*, vol. 97, pp. 882–888 (1989)). For example, adenosine has been shown to binibit superoxide release from neutrophils stimulated by chemoattractants such as the synthetic mimic of bacterial peptides, f-met-leu-phe (fMLP), and the complement component $C_5a$ (Cronstein, B. N., et al.,*J. Imnutol.*, vol. 135, pp. 1366–1371 (1985)). Adenosine can decrease the greatly enhanced oxidative burst of PMN (neutrophil) first primed with TNF-α (an inflammatory cytokine) and then stimulated by a second stimulus such as f-met-leu-phe (Sullivan, G. W., et al., *Clin. Res.*, vol. 41, p. 172A (1993)). There is evidence that in vivo adenosine has anti-inflammatory activity (Firestein, G. S., et al., *Clin. Res.*, vol. 41, p. 170A (1993); and Cronstein, B. N., et al., *Clin. Res.*, vol. 41, p. 244A (1993)). Additionally, it has been reported that adenosine can decrease the rate of HIV replication in a T-cell line (Sipka, S., et al., *Acta. Biochim. Biopys. Hung.*, vol. 23, pp. 75–82 (1988)).

It has been suggested that there is more than one subtype of adenosine receptor on neutrophils that have opposite effects on superoxide release (Cronstein, B. N., et al.,*J. Clin. Invest.*, vol. 85, pp. 1150–1157 (1990)). The existence of $A_{2A}$ receptor on neutrophils was originally demonstrated by Van Calker et al. (Van Calker, D., et al., *Eur. J. Pharmacology*, vol. 206, pp. 285–290 (1991)).

There has been progressive development of compounds that are more and more potent and selective as agonists of $A_{2A}$ adenosine receptors based on radioligand binding assays and physiological responses. Initially, compounds with little or no selectivity for $A_{2A}$ receptors were used, such as adenosine itself or 5'-carboxamides of adenosine, such as 5'-N-ethylcarboxamidoadenosine (NECA) (Cronstein, B. N., et al., *J. Immunol.*, vol. 135, pp. 1366–1371 (1985)). Later, it was shown that addition of 2-alkylamino substituents increased potency and selectivity, e.g. CV1808 and CGS21680 (Jarvis, M. F., et al., *J. Pharmacol. Exp. Ther.*, vol. 251, pp. 888–893 (1989)). 2-Alkoxy-substituted adenosine derivatives such as WRC-0090 are even more potent and selective as agonists on the coronary artery $A_{2A}$ receptor (Ukena, M., et al., *J. Med. Chem.*, vol. 34, pp. 1334–1339 (1991)). The 2-alkylhydrazino adenosine derivatives, e.g. SHA 211 (also called WRC-0474) have also been evaluated as agonists at the coronary artery $A_{2A}$ receptor (Niiya, K., et al., *J. Med. Chem.*, vol. 35, pp. 45574561 (1992)).

There is one report of the combination of relatively nonspecific adenosine analogs, R-phenylisopropyladenosine (R-PIA) and 2-chloroadenosine (Cl-Ado) with a phosphodiesterase (PDE) inhibitor resulting in a lowering of neutrophil oxidative activity (lannone, M. A., et al., in *Topics and Perspectives in Adenosine Research*, E. Gerlach et al., Eds., Springer-Verlag, Berlin, pp. 286–298 (1987)). However, R-PIA and Cl-Ado analogs are actually more potent activators of $A_1$ adenosine receptors than of $A_{2A}$ adenosine receptors and, thus, are likely to cause side effects due to activation of $A_1$ receptors on cardiac muscle and other tissues causing effects such as "heart block".

Linden et al. Ser. No. 08/272,821 is based on the discovery that inflammatory diseases may be effectively treated by the administration of drugs which are selective agonists of $A_{2A}$ adenosine receptors, preferably in combination with a phosphodiesterase inhibitor. An embodiment of the Linden et al. invention provides a method for treating inflammatory diseases by administering an effective amount of an $A_{2A}$ adenosine receptor of the following formula:

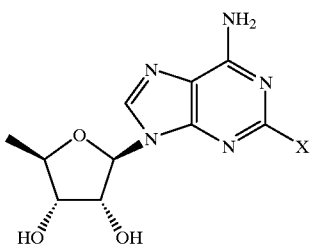

(I)

wherein X is a group selected from the group consisting of —$OR^1$, —$NR^2R^3$, and —NH—N=$R^4$;
  wherein $R^1$ is $C_{1-4}$-alkyl; $C_{1-4}$-alkyl substituted with one or more $C_{1-4}$-alkoxy groups, halogens (-fluorine, chlorine, or bromine), hydroxy groups, amino groups, mono($C_{1-4}$-alkyl)amino groups, di($C_{1-4}$,-alkyl)amino groups, or $C_{6-10}$-aryl groups (wherein the aryl groups may be substituted with one or more halogens (fluorine, chlorine, or bromine), $C_{1-4}$-alkyl groups, hydroxy groups, amino groups, mono($C_{1-4}$-alkyl)amino groups, or di($C_{1-4}$ alkyl) amino groups); $C_{6-10}$-aryl; or $C_{6-10}$-aryl substituted with one or more halogens (fluorine, chlorine, or bromine), hydroxy groups; amino groups, mono($C_{1-4}$alkyl)amino groups, or di($C_{1-4}$-alkyl)amino groups, or $C_{1-4}$-alkyl groups;
  one of $R^2$ and $R^3$ has the same meaning as $R^1$ and the other is hydrogen;
  $R^4$ is a group having the formula:

wherein each of $R^5$ and $R^6$ independently may be hydrogen, $C_{3-7}$-cycloalkyl, or any of the meanings of $R^1$, provided that $R^5$ and $R^6$ are not both hydrogen; and R is —$CH_2OH$, —$CH_2H$, —$CO_2R^7$, or —C(=O)$NR^8R^9$; wherein $R^7$ has the same meaning as $R^1$ and wherein $R^8$ and $R^9$ have the same meanings as $R^5$ and $R^6$ and $R^8$ and $R^9$ may both be hydrogen.

In a preferred embodiment, the Linden et al. invention involves the admInistration of a Type IV phosphodiesterase (PDE) inhibitor in combination with the $A_{2A}$ adenosine receptor agonist. The Type IV phosphodiesterase (PDE) inhibitor can be racemic and optically active 4-(polyalkoxyphenyl)-2—pyrrolidones of the following formula:

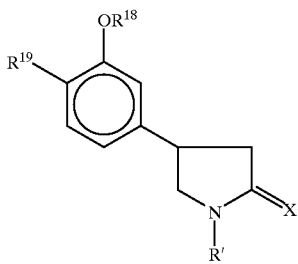

(disclosed and described in U.S. Pat. No. 4,193,926) wherein $R^{18}$ and $R^{19}$ each are alike or different and are hydrocarbon radicals having up to 18 carbon atoms with at least one being other than methyl, a heterocyclic ring, or alkyl of 1–5 carbon atoms which is substituted by one or more of halogen atoms, hydroxy, carboxy, alkoxy, alkoxycarbonyl or an amino group; amino; R' is a hydrogen atom, alkyl, aryl or acyl; and X is an oxygen atom or a sulfur atom.

Rolipram is an example of a suitable Type IV phosphodiesterase or PDE inhibitor included within the above formula. Rolipram has the following structure:

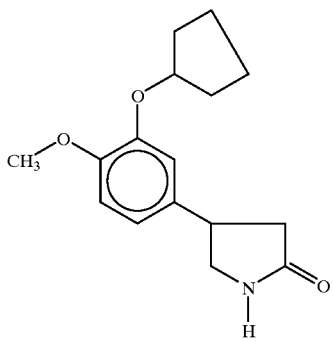

The present invention is based on the inventors' discovery that improved effective treatment of inflammatory disease is achieved by the administration of certain agonists of $A_{2A}$ adenosine receptors in combination with rolipram or rolipram derivatives that are Type IV phosphodiesterase or PDE inhibitors.

SUMMARY OF THE INVENTION

Accordingly, one object of the present invention is to provide a novel and improved method for treating inflammatory diseases.

It is another object of the present invention to provide novel and improved compositions for the treatment of inflammatory disease.

These and other objects, which will become better understood during the course of the following detailed description, have been achieved by the inventors' discovery of improved compositions and methods for effectively treating inflammatory diseases by administration of an agonist of an $A_{2A}$ adenosine receptor in combination with rolipram or a rolipram derivative that is a Type IV phosphodiesterase (PDE) inhibitor.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

Figure 3:
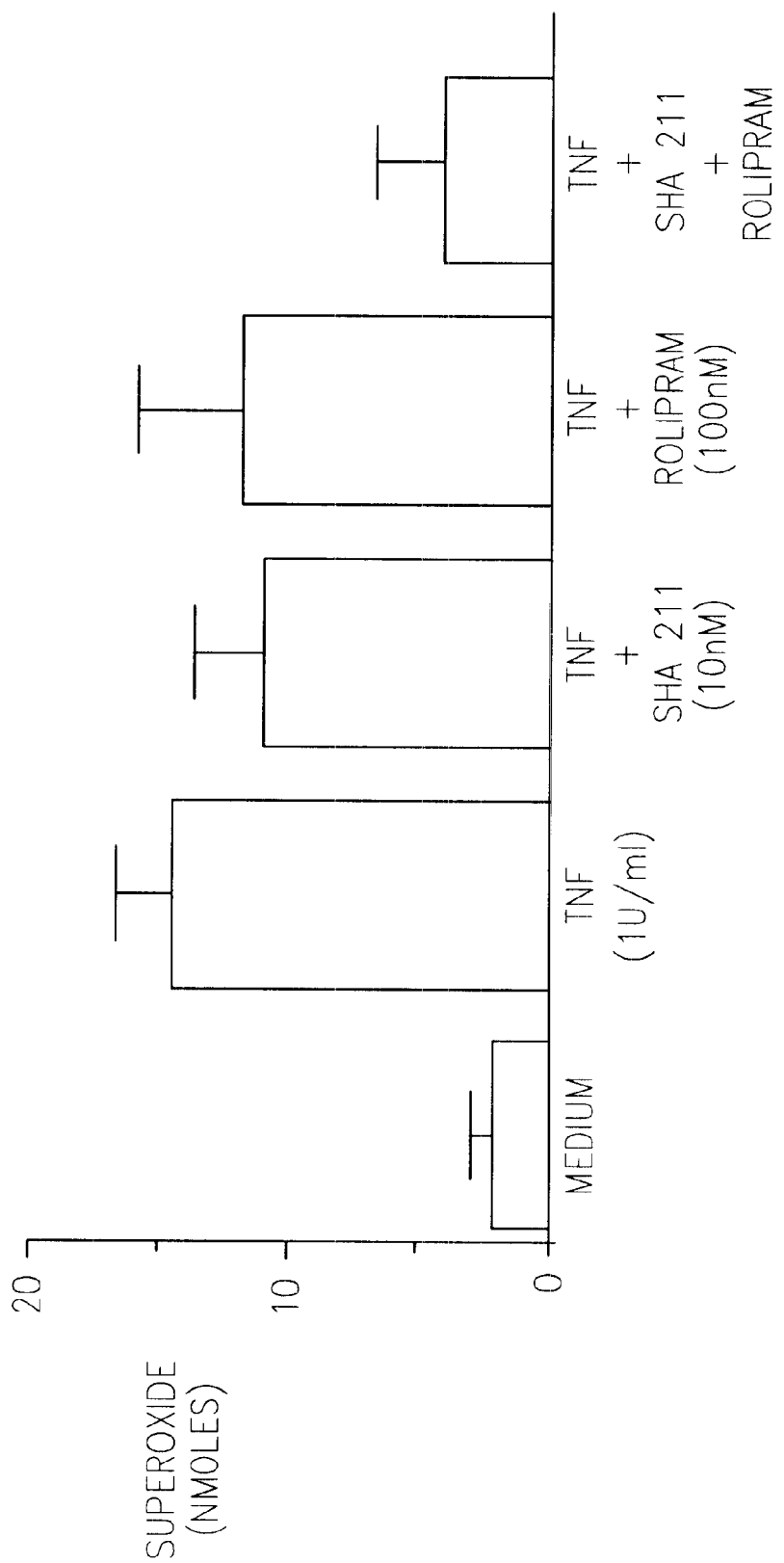
Figure 4:
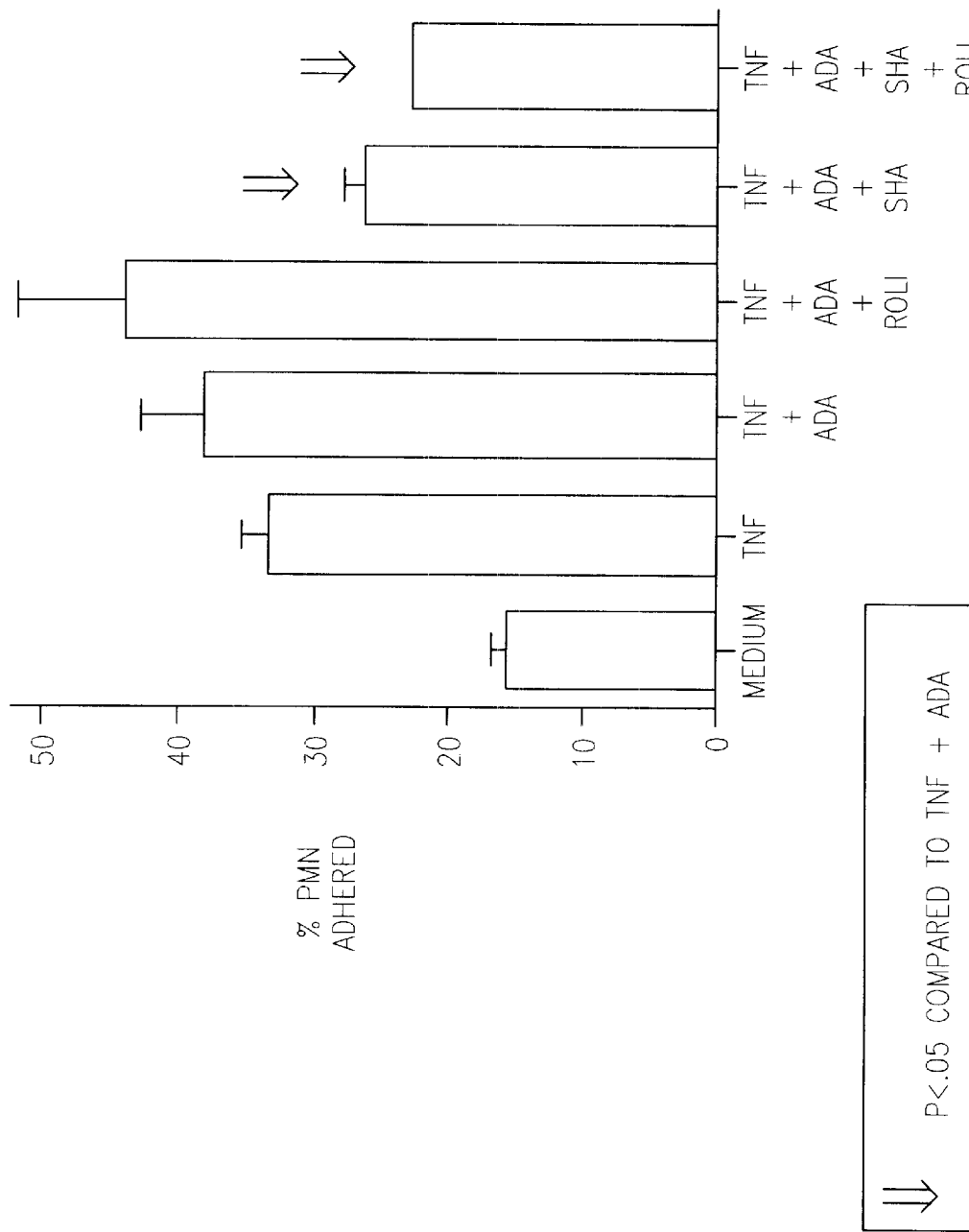
Figure 5A:
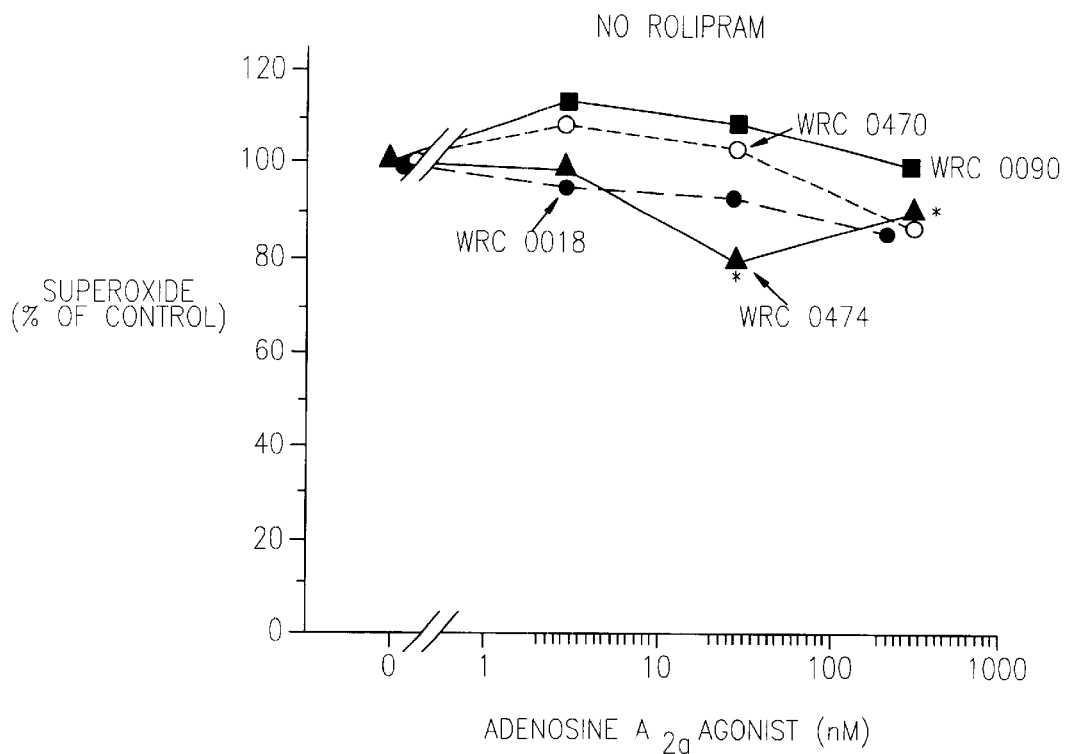
Figure 5B:
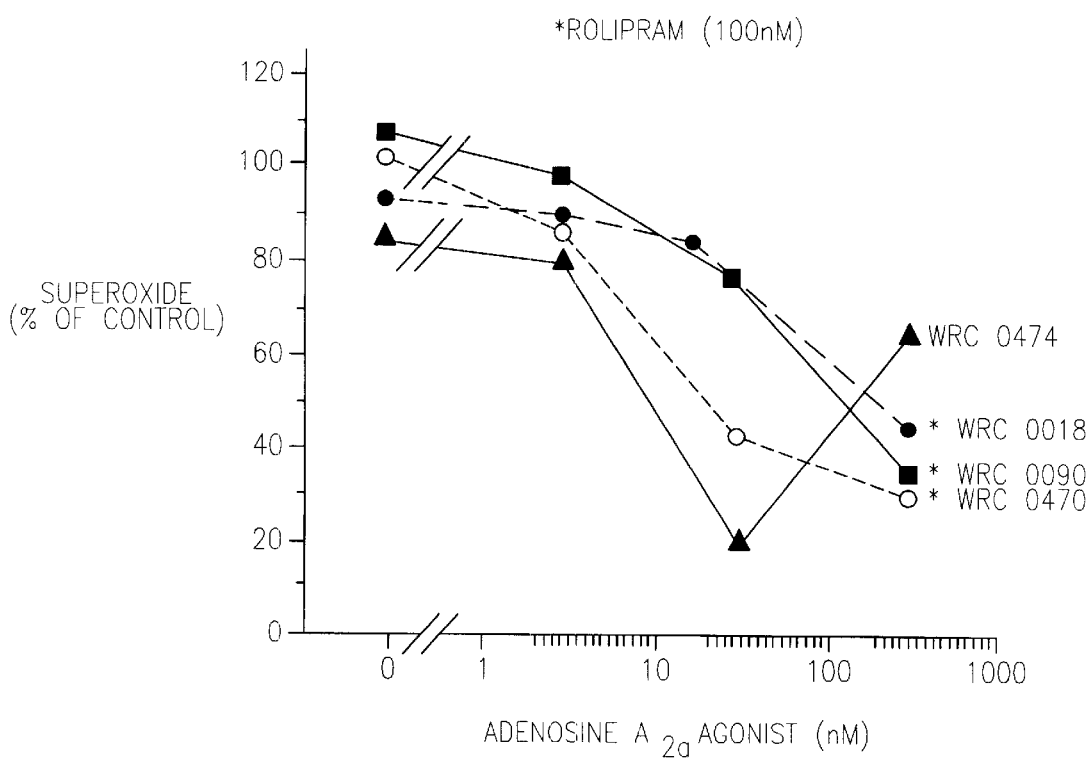
Figure 6:
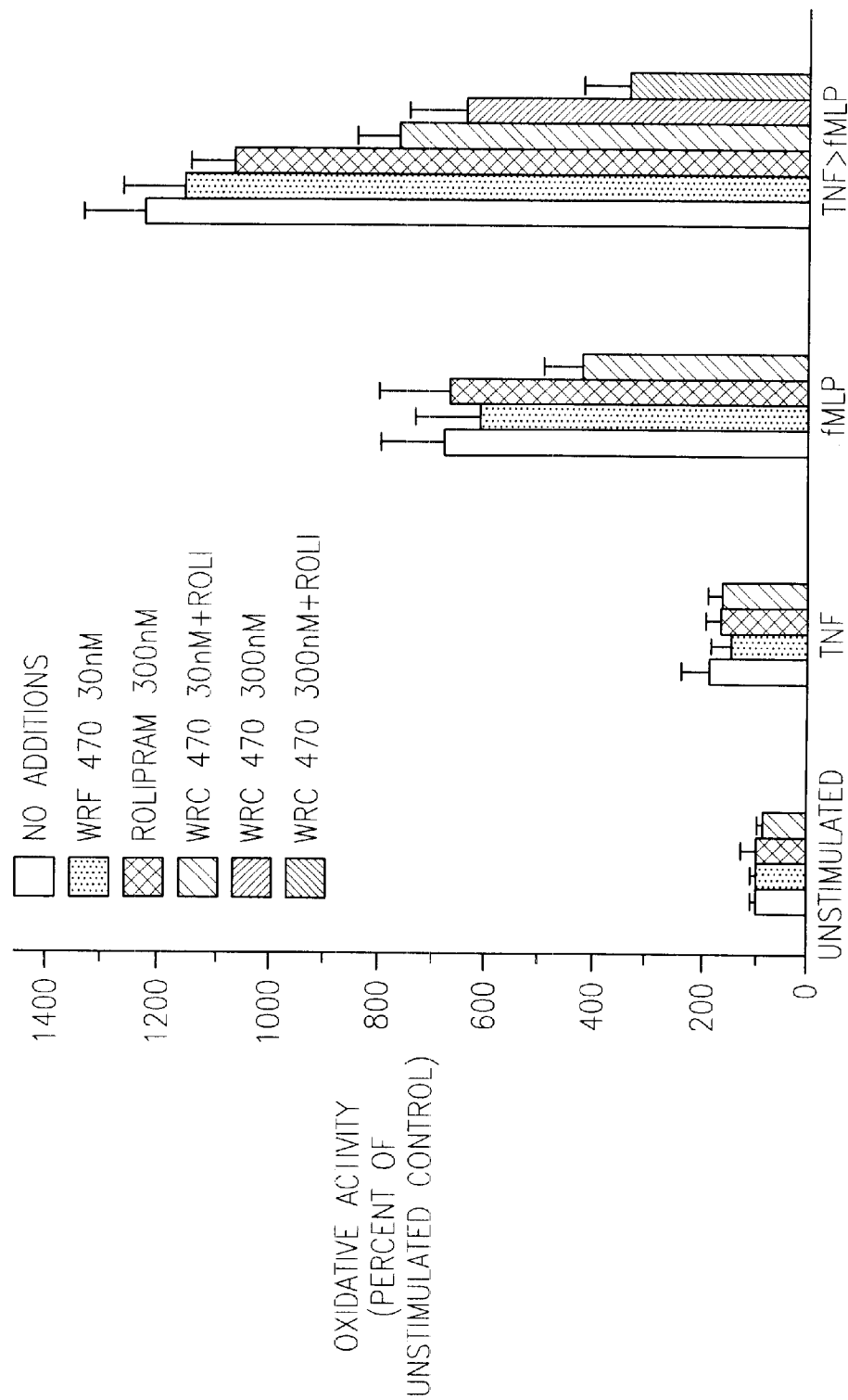
Figure 7A:
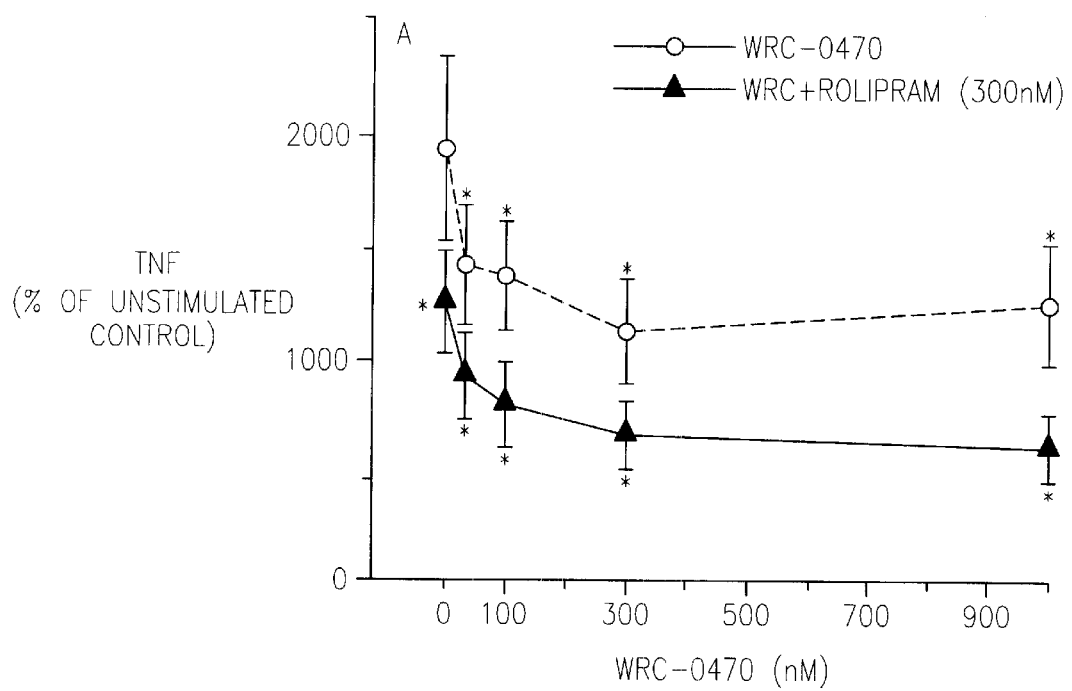
Figure 7B:
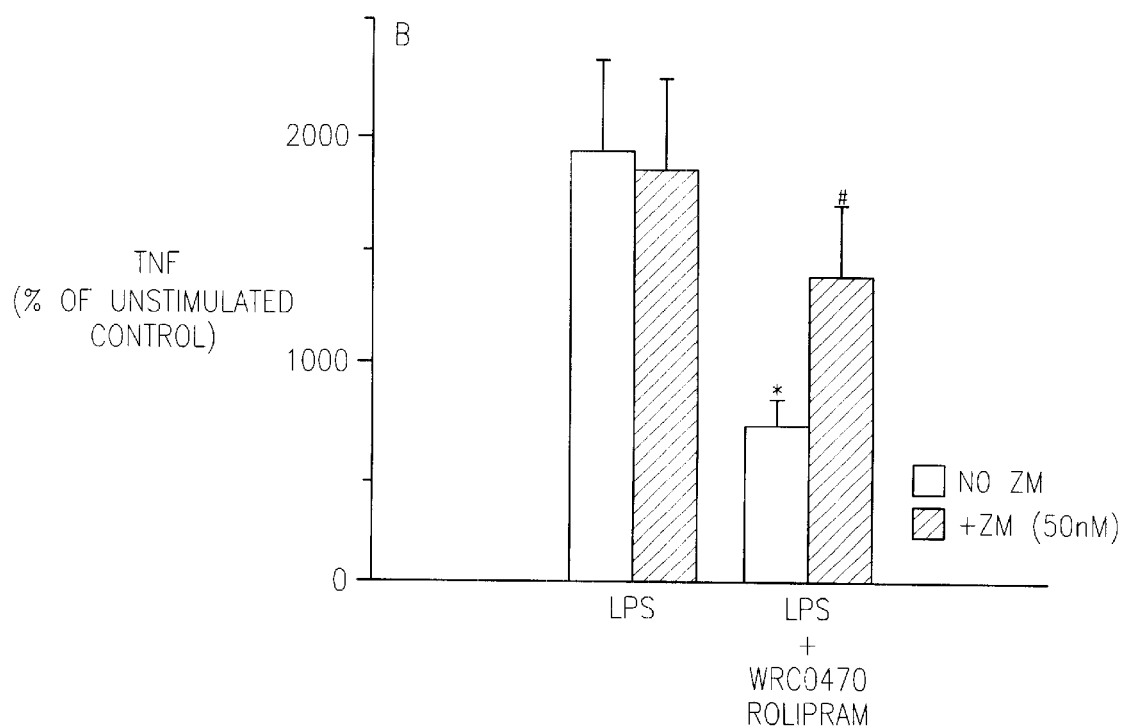

FIG. 3 illustrates the synergistic effect of WRC-0474 [SHA 211] and rolipram in inhibiting TNFα-stimulated adherent PMN superoxide release;

FIG. 4 illustrates the effect of WRC-0474[SHA 211] and rolipram on TNFα-stimulated PMN adherence to a fibrinogen coated surface;

FIG. 5 illustrates synergy between $A_{2A}$ adenosine receptor agonists and Rolipram in inhibiting superoxide release from TNFα-stimulated adherent human neutrophils;

FIG. 6 illustrates the effects of WRC-0470 and rolipram on the oxidative activity of neutrophils in whole blood;

FIGS. 7A and 7B illustrates the effects of WRC-0470 and rolipram on the release of TNFα from adherent human monocytes and that this activity is dependent on binding of the adenosine agonist to $A_{2A}$ adenosine receptors.

Figure 8:
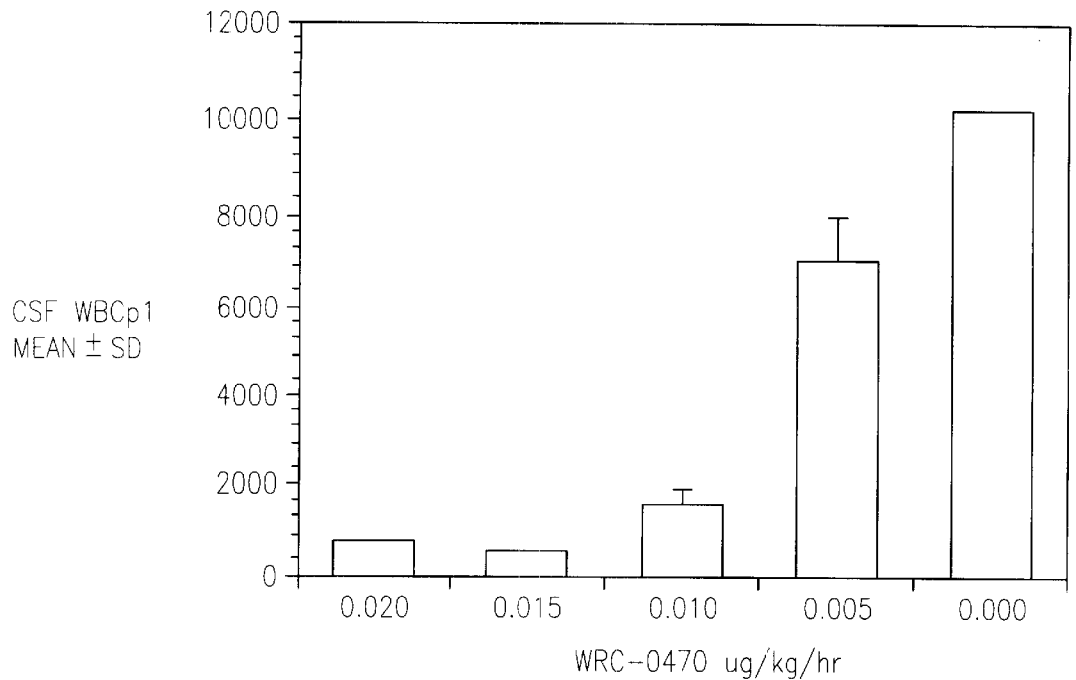

FIG. 8 illustrates the effect of WRC-0470 on white blood cell pleocytosis in rats.

Figure 9:
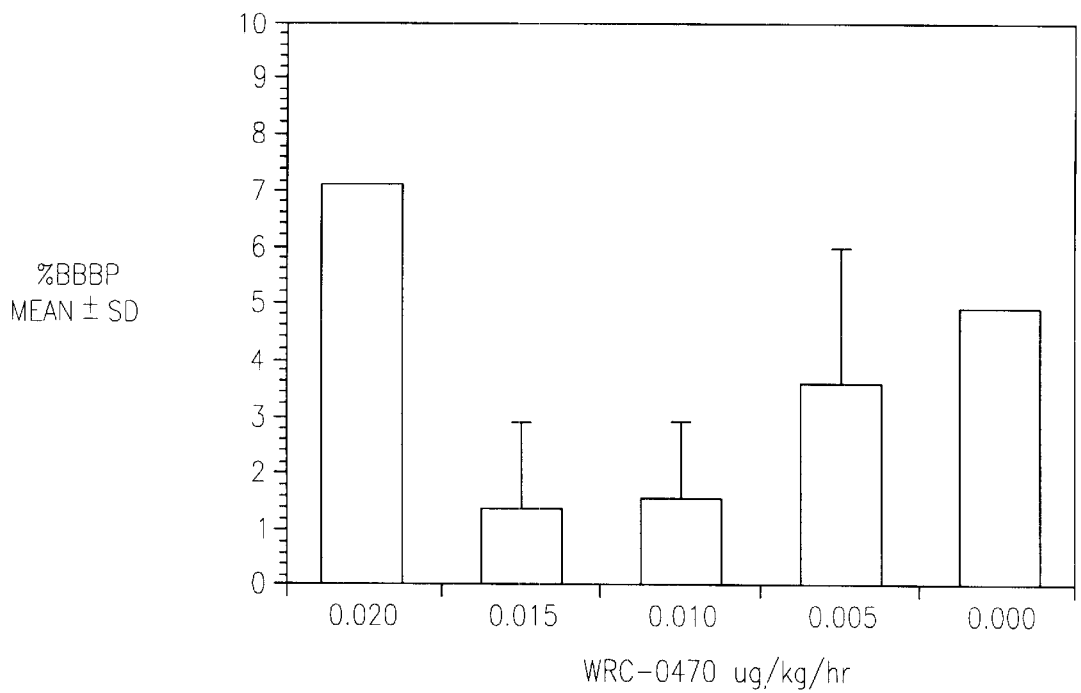
Figure 10:
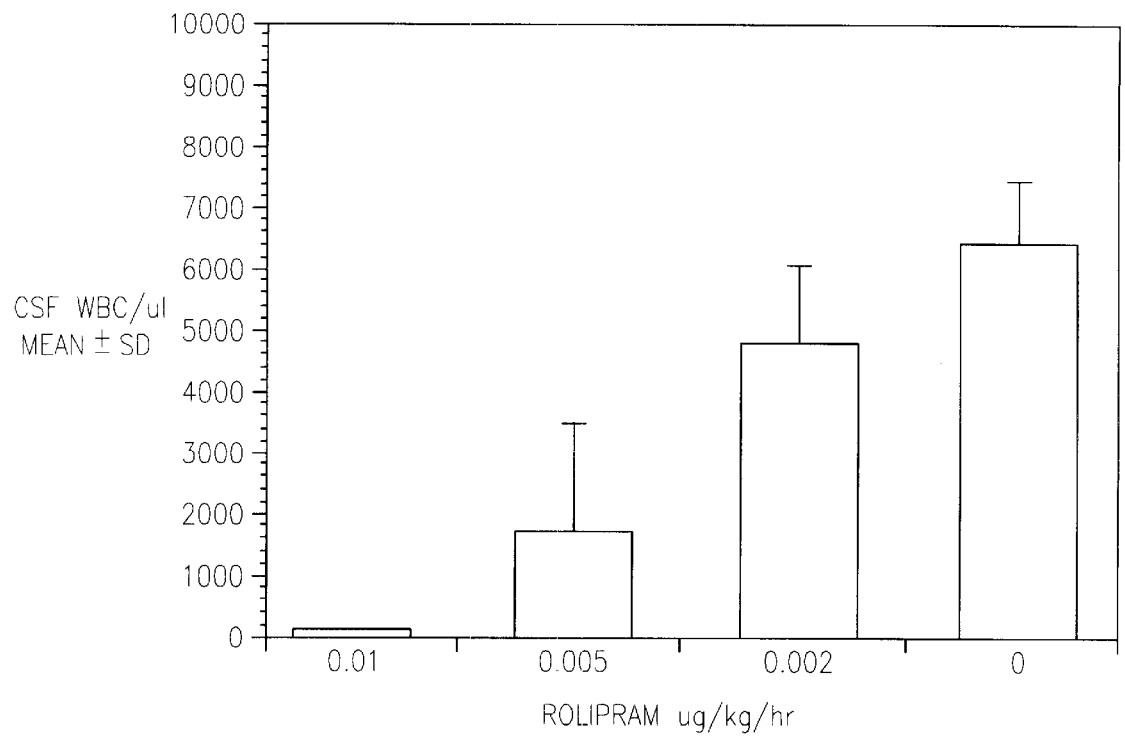
Figure 11:
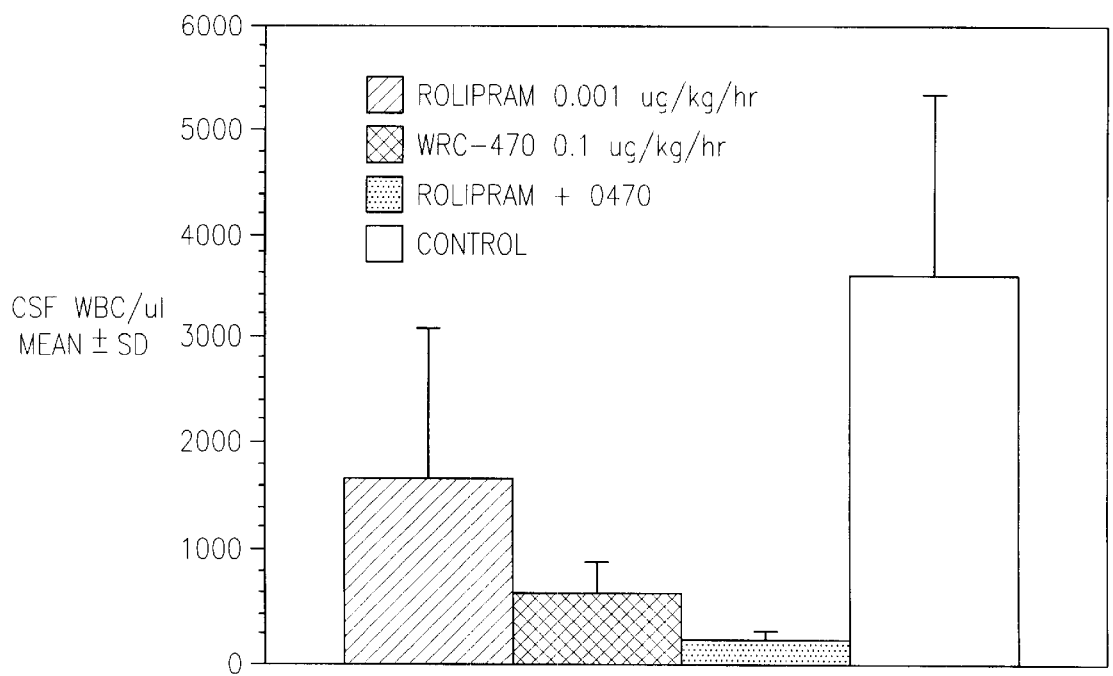

FIG. 9 illustrates the effect of WRC-0470 on blood-brain-barrier permeability in rats;

FIG. 10 illustrates the effect of rolipram on white blood cell pleocytosis in rats; and FIG. 11 illustrates the combined effect of WRC-0470 and rolipram on white blood cell pleocytosis in rats.

DETAILED DESCRIPTION OF THE PREFERRED EMBODIMENTS

Thus, in a first embodiment, the present invention provides a method for treating inflammatory diseases by administering an effective amount of a compound of formula (I):

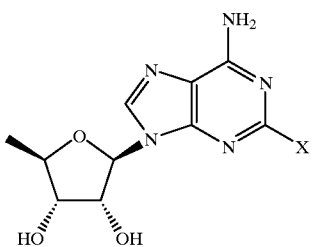

(I)

wherein X is a group selected from the group consisting of —$OR^1$, —$NR^2R^3$, and —NH—N=$R^4$;

wherein $R^1$ is $C_{1-4}$-alkyl; $C_{1-4}$-alkyl substituted with one or more $C_{1-4}$-alkoxy groups, halogens (-fluorine, chlorine, or bromine), hydroxy groups, amino groups, mono($C_{1-4}$-alkyl)amino groups, di($C_{1-4}$-alkyl)amino groups, or $C_{6-10}$-aryl groups (wherein the aryl groups may be substituted with one or more halogens (fluorine, chlorine, or bromine), $C_{1-4}$-alkyl groups, hydroxy groups, amino groups, mono($C_{1-4}$-alkyl)anino groups, or di($C_{1-4}$ alkyl) amino groups); $C_{1-6}$-aryl; or $C_{6-4}$-aryl substituted with one or more halogens (fluorine, chlorine, or bromine), hydroxy groups, amino groups, mono($C_{1-4}$-alkyl)amino groups, or di($C_{1-4}$ alkyl)amino groups, or $C_{1-4}$-alkyl groups;

one of $R^2$ and $R^3$ has the same meaning as $R^1$ and the other is hydrogen;

$R^4$ is a group having the formula (II)

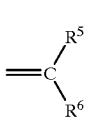

(II)

wherein each of $R^5$ and $R^6$ independently may be hydrogen, $C_{3-7}$-cycloalkyl, or any of the meanings of $R^1$, provided that $R^5$ and $R^6$ are not both hydrogen;

Examples of suitable $C_{6-10}$-aryl groups include phenyl and naphthyl.

Preferably the compound of formula (I) has X being a group of the formula (III)

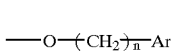

(III)

wherein n is an integer from 1–4, preferably 2, and Ar is a phenyl group, tolyl group, naphthyl group, xylyl group, or mesityl group. Most preferably Ar is a para-tolyl group and n=2.

Even more preferably, the compound of formula (IV) has X being a group of the formula (I)

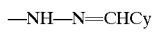

(IV)

wherein Cy is a $C_{3-7}$-cycloalkyl group, preferably cyclohexyl or a $C_{1-4}$ alkyl group, preferably isopropyl.

Specific examples of such compounds of formula (I) include WRC-0470, WRC-0474 [SHA 211], WRC-0090 and WRC-0018, shown below:

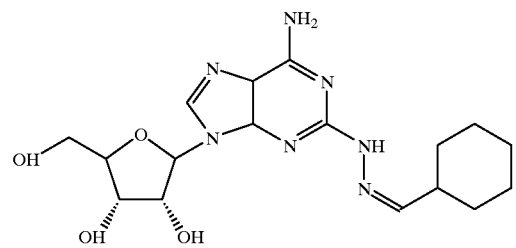

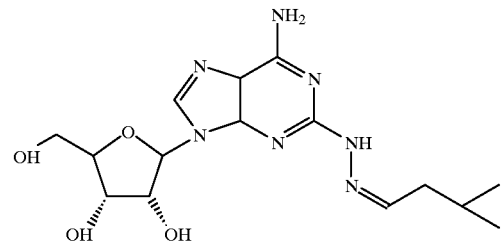

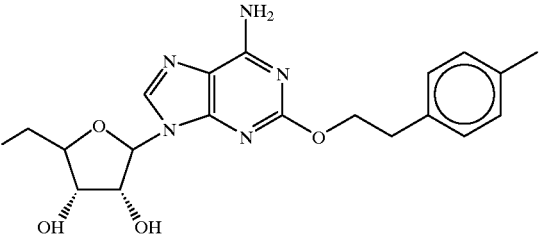

and

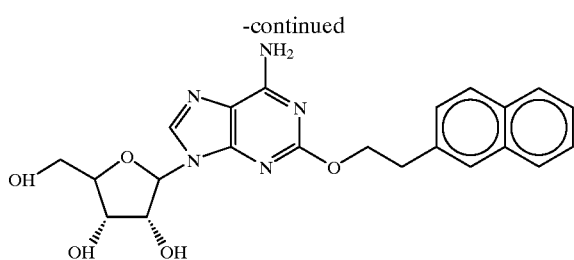

Of these specific examples, WRC-0474[SHA 211] and WRC-0470 are particularly preferred.

Such compounds may be synthesized as described in: Hutchinson, A. J., et al., *J. Pharmacol. ExD. Ther.*, vol. 251, pp. 47–55 (1989); Olsson, R. A., et al., *J. Med. Chem.*, vol. 29, pp. 1683–1689 (1986); Bridges, A. J., et al., *J. Med. Chem.*, vol. 31, pp. 1282–1285 (1988); Hutchinson, A. J., et al., *J. Med. Chem.*, vol. 33, pp. 1919–1924 (1990); Ukena, M., etal., *J. Med. Chem.*, vol. 34, pp. 1334–1339 (1991); Francis, J. E., et al., *J. Med. Chem.*, vol. 34, pp. 2570–2579 (1991); Yoneyama, F., et al., *Eur. J. Pharmacol.*, vol. 213, pp. 199–204 (1992); Peet, N. P., et al., *J. Med. Chem.*, vol. 35, pp. 3263–3269 (1992); and Cristalli, G., et al., *J. Med. Chem.*, vol. 35, pp. 2363–2368 (1992); all of which are incorporated herein by reference.

The present method includes the administration of a Type IV phosphodiesterase (PDE) inhibitor in combination with the compound of formula (I). Examples of Type IV phosphodiesterase inhibitors include those disclosed in U.S. Pat. No. 4,193,926, and WO 92-079778, and Molnar-Kimber, K. L., et al., *J. Immunol.*, vol. 150, p. 295A (1993), all of which are incorporated herein by reference.

Specifically, the suitable Type IV phosphodiesterase (PDE) inhibitors include racemic and optically active 4-(polyalkoxyphenyl)-2-pyrrolidones of general formula (V)

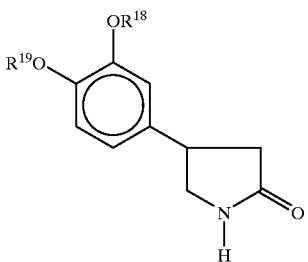

(V)

(disclosed and described in U.S. Pat. No. 4,193,926) wherein $R^{18}$ and $R^{19}$ each are alike or different and are hydrocarbon radicals having up to 18 carbon atoms with at least one being other than methyl, a heterocyclic ring, or alkyl of 1–5 carbon atoms which is substituted by one or more of halogen atoms, hydroxy, carboxy, alkoxy, alkoxycarbonyl or an amino group or amino.

Examples of hydrocarbon $R^{18}$ and $R^{19}$ groups are saturated and unsaturated, straight-chain and branched alkyl of 1–18, preferably 1–5, carbon atoms, cycloalkyl and cycloalkylalkyl, preferably of 3–7 carbon atoms, and aryl and aralkyl, preferably of 6–10 carbon atoms, especially monocyclic.

Examples of alkyl are methyl, ethyl, propyl, isopropyl, butyl, isobutyl, tert-butyl, pentyl, 2-methylbutyl, 2,2-dimethylpropyl, hexyl, heptyl, octyl, nonyl, 1,2dimethylheptyl, decyl, undecyl, dodecyl and stearyl, with the proviso that when one of $R^{18}$ and $R^{19}$ is methyl, the other is a value other than methyl. Examples of unsaturated alkyl groups are alkenyl and alkynyl, e.g., vinyl, 1-propenyl, 2-propenyl, 2-propynyl and 3-methyl-2-propenyl.

Examples of cycloalkyl and cycloalkylalkyl which preferably contain a total of 3–7 carbon atoms are cyclopropyl, cyclopropylmethyl, cyclopentyl and cyclohexyl.

Examples of aryl and aralkyl are phenyl and benzyl, which are preferred, and tolyl, xylyl, naphthyl, phenethyl and 3phenylpropyl.

Examples of heterocyclic $R^{18}$ and $R^{19}$ groups are those wherein the heterocyclic ring is saturated with 5 or 6 ring members and has a single 0, S or N atom as the hetero atom, e.g., 2- and 3-tetrahydrofaryl, 2 and 3-tetrahydropyranyl, 2- and 3-tetrahydrothiophenyl, pyrrolidino, 2- and 3-pyrrolidyl, piperidino, 2-, 3- and 4-piperidyl, and the corresponding N-alkyl-pyrrolidyl and piperidyl wherein alkyl is of 1–4 carbon atoms. Equivalents are heterocyclic rings having fewer or more, e.g., 4 and 7, ring members, and one or more additional hetero atoms as ring members, e.g., morpholino, piperazino and N-alkylpiperazino.

Examples of substituted alkyl $R^{18}$ and $R^{19}$ groups, preferably of 1–5 carbon atoms, are those mono- or polysubstituted, for example, by halogen, especially fluorine, chlorine and bromine. Specific examples of such halogen-substituted alkyl are 2-chloroethyl, 3-chloropropyl, 4-bromobutyl, difluoromethyl, trifluoromethyl, 1,1,2-trifluoro-2-chloroethyl, 3,3,3-trifluoropropyl, 2,2,3,3,3-pentafluoropropyl and 1,1,1,3,3,3-hexafluoro-2-propyl. Examples of other suitable substituents for such alkyl groups are hydroxy groups, e.g., 2-hydroxyethyl or 3-hydroxypropyl; carboxy groups, e.g., carboxymethyl or carboxyethyl; alkoxy groups, wherein each alkoxy group contains 1–5 carbon atoms, e.g., ethoxymethyl, isopropoxymethyl, 2-methoxyethyl, 2-isopropoxyethyl, 2-butyoxyethyl, 2-isobutyoxyethyl, and 3—pentoxypropyl.

Also suitable as preferably terminal-positioned substituents on alkyl groups of 1–5 carbon atoms are alkoxycarbonyl of 1–5 carbon atoms in the alkoxy group. Examples of such alkoxycarbonyl substituted alkyl-groups are ethoxycarbonylmethyl and 2-butoxycarbonylethyl.

Alkyl groups of 1–5 carbon atoms can also be substituted, e.g., in the β, γ and preferably terminal position with amino groups wherein the nitrogen atom optionally is mono- or disubstituted by alkyl, preferably of 1–5 carbon atoms, or is part of a 4- to 7-membered ring.

A Rolipram and its analogues are specific examples of preferred Type IV phosphodiesterase inhibitors.

Examples of inflammatory diseases which may be treated according to the present invention include:

autoimmune diseases such as lupus erythenatosis, multiple sclerosis, type I diabetes mellits, Crohn's disease, ulcerative colitis, inflammatory bowel disease, osteoporosis, arthritis, allergic diseases such as asthma, infectious diseases such as sepsis, septic shock, infectious arthritis, endotoxic shock, gram negative shock, toxic shock,cerebral malarial bacterial meningitis, adult respiratory distress syndrome (ARDS), TNFα-enhanced HIV replication and TNFα inhibition of reverse transcriptase inhibitor activity, wasting diseases (cachexia secondary to cancer and HIV), skin diseases like psoriasis, contact dermatitis, eczema, infectious skin ulcers, cellulitis, organ transplant rejection (including bone marrow, kidney, liver, lung, heart, skin rejection), graft versus host disease, adverse effects from amphotericin B treatment, adverse effects from interleukin-2 treatment, adverse effects from OKT3 treatment, adverse effects from GMCSF treatment, adverse effects of cyclosporine treatment and adverse effects of aminoglycoside treatment, ischemia, mucositis, infertility from endometriosis, circulatory diseases induced or exacerbated by an inflammatory response such as atherosclerosis, peripheral vascular disease, restenosis following angioplasty, inflammatory aortic aneurysm, ischemia/reperfusion damage, vasculitis, stroke, congestive heart failure, hemorrhagic shock, vasospasm following subarachnoid hemorrhage, vasospasm following cerebrovascular accident, pleuritis, pericarditis, and encephalitis.

The exact dosage of the compound of formula (I) to be administered will, of course, depend on the size and condition of the patient being treated, the exact condition being treated, and the identity of the particular compound of formula (I) being administered. However, a suitable dosage of the compound of formula (I) is 0.5 to 100 $\mu$g/kg of body weight, preferably 1 to 10 $\mu$g/kg of body weight. Typically, the compound of formula (I) will be administered from 1 to 8, preferably 1 to 4, times per day.

The preferred mode of administration of the compound of formula (I) may also depend on the exact condition being treated. However, most typically, the mode of administration will be oral, topical, intravenous, parenteral, subcutaneous, or intramuscular injection.

Of course, it is to be understood that the compound of formula (I) may be administered in the form of a pharmaceutically acceptable salt. Examples of such salts include acid addition salts. Preferred pharmaceutically acceptable addition salts include salts of mineral acids, for example, hydrochloric acid, sulfuric acid, nitric acid, and the like; salts of monobasic carboxylic acids, such as, for example, acetic acid, propionic acid, and the like; salts of dibasic carboxylic acids, such as maleic acid, fumaric acid, oxalic acid, and the like; and salts of tribasic carboxylic acids, such as, carboxysuccinic acid, citric acid, and the like. In the compounds of formula (I) in which R is —$CO_2H$, the salt may be derived by replacing the acidic proton of the —$CO_2H$ group with a cation such as $Na^+$, $K^+$, $NH^+_4$ mon-, di, tri, or tetra($C_{1-4}$-alkyl)ammonium, or mono-, di-, tri-, or tetra($C_{2-4}$alkanol)ammonium.

It is also to be understood that many of the compounds of formula (I) may exist as various isomers, enantiomers, and diastereomers and that the present invention encompasses the administration of a single isomer, enantiomer, or diastereomer in addition to the administration of mixtures of isomers, enantiomers, or diastereomers.

The compounds of formula (I) can be administered orally, for example, with an inert diluent with an edible carrier. They can be enclosed in gelatin capsules or compressed into tablets. For the purpose of oral therapeutic administration, the compounds can be incorporated with excipients and used in the form of tablets, troches, capsules, elixirs, suspensions, syrups, waters, chewing gums, and the like. These preparations should contain at least 0.5% by weight of the compound of formula (I), but the amount can be varied depending upon the particular form and can conveniently be between 4.0% to about 70% by weight of the unit dosage. The amount of the compound of formula (I) in such compositions is such that a suitable dosage will be obtained. Preferred compositions and preparations according to the present invention are prepared so that an oral dosage unit form contains between about 30 $\mu$g and about 5 mg, preferably between 50 to 500 $\mu$g, of active compound.

Tablets, pills, capsules, troches, and the like can contain the following ingredients: a binder, such as microcrystalline cellulose, gum tragacanth or gelatin; an excipient, such as starch or lactose; a disintegrating agent, such as alginic acid, Primogel, corn starch, and the like; a lubricant, such as magnesium stearate or Sterotes; a glidant, such as colloidal silicon dioxide; a sweetening agent, such as sucrose, saccharin or aspartame; or flavoring agent, such as peppermint, methyl salicylate, or orange flavoring. When the dosage unit form is a capsule it can contain, in addition to the compound of formula (I), a liquid carrier, such as a fatty oil.

Other dosage unit forms can contain other materials that modify the physical form of the dosage unit, for example, as coatings. Thus, tablets or pills can be coated with sugar, shellac, or other enteric coating agents. A syrup may contain, in addition to the active compounds, sucrose as a sweetening agent and preservatives, dyes, colorings, and flavors. Materials used in preparing these compositions should be pharmaceutically pure and non-toxic in the amounts used.

For purposes of parenteral therapeutic administration, the compounds of formula (I) can be incorporated into a solution or suspension. These preparations should contain at least 0.1% of the aforesaid compound, but may be varied between 0.5% and about 50% of the weight thereof. The amount of active compound in such compositions is such that a suitable dosage will be obtained. Preferred compositions and preparations according to the present invention are prepared so that a parenteral dosage unit contains between 30 $\mu$g to 5 mg, preferably between 50 to 500 $\mu$g, of the compound of formula (I).

Solutions or suspensions of the compounds of formula (I) can also include the following components: a sterile diluent, such as water for injection, saline solution, fixed oils, polyethylene glycols, glycerine, propylene glycol or other synthetic solvents: antibacterial agents, such as benzyl alcohol or methyl parabens; antioxidants, such as ascorbic acid or sodium bisulfite; chelating agents, such as ethylenediaminetetraacetic acid; buffers, such as acetates, citrates or phosphates; and agents for the adjustment of tonicity, such as sodium chloride or dextrose. The parenteral preparation can be enclosed in ampoules, disposable syringes or multiple dose vials made of glass or plastic.

Effective amounts of the Type IV phosphodiesterase inhibitor can be administered to a subject by any one of various methods, for example, orally as a capsule or tablets, topically, or parenterally in the form of sterile solutions. The Type IV phosphodiesterase inhibitors, while effective themselves, can be formulated and administered in the form of their pharmaceutically acceptable addition salts for purposes of stability, convenience of crystallization, increased solubility, and the like.

Preferred pharmaceutically acceptable addition salts include salts of mineral acids, for example, hydrochloric acid, sulfuric acid, nitric acid, and the like; salts of monobasic carboxylic acids, such as, for example, acetic acid, propionic acid, and the like; salts of dibasic carboxylic acids, such as maleic acid, fumaric acid, oxalic acid, and the like; and salts of tribasic carboxylic acids, such as, carboxysuccinic acid, citric acid, and the like.

The Type IV phosphodiesterase may be administered in the form of a pharmaceutical composition similar to those described above in the context of the compound of formula (I).

While dosage values will vary with the specific disease condition to be alleviated, good results are achieved when the Type IV phosphodiesterase inhibitor is administered to a subject requiring such treatment as an effective oral, parenteral or intravenous dose as described below.

For oral administration, the amount of active agent per oral dosage unit usually is 0.1–20 mg, preferably 0.5–10 mg.

The daily dosage is usually 0.1–50 mg, preferably 1–30 mg. p.o. For parenteral application, the amount of active agent per dosage unit is usually 0.005–10 mg, preferably 0.01–5 mg. The daily dosage is usually 0.01–20 mg, preferably 0.02–5 mg i.v. or i.m.

With topical administration, dosage levels and their related procedures would be consistent with those known in the art, such as those dosage levels and procedures described in U.S. Pat. No. 5,565,462 to Eitan et al., which is incorporated herein by reference.

It is to be understood, however, that for any particular subject, specific dosage regimens should be adjusted to the individual need and the professional judgement of the person administering or supervising the administration of the Type IV phosphodiesterase inhibitor. It is to be further understood that the dosages set forth herein are exemplary only and that they do not, to any extent, limit the scope or practice of the present invention.

In a particularly preferred embodiment, the compound of formula (I) and the Type IV phosphodiesterase inhibitor are coadministered together in a single dosage unit. The compound of formula (I) and the type IV phosphodiesterase inhibitor may be administered in the same type of pharmaceutical composition as those described above in the context of the compound of formula (I).

By coadministering a Type IV phosphodiesterase inhibitor with the agonist of the $A_{2A}$ adenosine receptor it is possible to dramatically lower the dosage of the $A_{2A}$ adenosine receptor agonist and the Type IV phosphodiesterase inhibitor due to a synergistic effect of the two agents. Thus, in the embodiment involving coadministration of the $A_{2A}$ adenosine receptor agonist with the type IV phosphodiesterase inhibitor, the dosage of the $A_{2A}$ adenosine receptor agonist may be reduced by a factor of 5 to 10 from the dosage used when no type IV phosphodiesterase inhibitor is administered. This reduces the possibility of side effects.

The present invention will now be described in more detail in the context of the coadministration of WRC-0470, WRC-0474[SHA 211], WRC-0090 or WRC-0018 and rolipram. However, it is to be understood that the present invention may be practiced with other compounds of formula (I) and other Type IV phosphodiesterase inhibitors of formula (V).

The present studies establish that anti-inflammatory doses have no toxic effects in animals; the effect of WRC0470 to inhibit neutrophil activation is synergistic with rolipram; and intravenous infusion of WRC-0470 profoundly inhibits extravasation of neutrophils in an animal model of inflammation, an action also synergistic with rolipram. Further, the present studies establish that activation of $A_{2A}$ receptors on human monocytes strongly inhibits TNFα (an inflamatory cytokine) release. This mechanism further contributes to the anti-inflamatory action of the $A_{2A}$ adenosine receptor agonists of the present invention.

Other features of the invention will become apparent in the course of the following descriptions of exemplary embodiments which are given for illustration of the invention and are not intended to be limiting thereof.

EXAMPLES

Materials and Methods

Materials: f-Met-Leu-Phe(fMLP), luminol, and trypan blue were from Sigma Chemical. Ficoll-hypaque was purchased from Flow Laboratories (McLean, A) and Los Alamos Diagnostics (Los Alamos, N. Mex.). Hanks balanced salt solution (HBSS), and limulus amebocyte lysate assay kit were from Whittaker Bioproducts (Walkersville, Md.). Human serum albumin (HSA) was from Cutter Biological (Elkhart, Ind.). Recombinant human tumor necrosis factor-alpha was supplied by Dianippon Pharmaceutical Co. Ltd. (Osaka, Japan). ZM241385 was a gidt of Dr. Simon Poucher, Zeneca Pharmaceuticals (Chesire, England).

Leukocyte Preparation: Purified PMN (~98% PMN and >95% viable by trypan blue exclusion) containing <1 platelet per 5 PMN and <50 pg/ml endotoxin (limulus amebocyte lysate assay) were obtained from normal heparinized (10 Units/ml) venous blood by a one step ficoll-hypaque separation procedure (Ferrante, A., et al., J. Immunol. Meth., vol. 36, p. 109, (1980)). Residual RBC were lysed by hypotonic lysis with iced 3 ml 0.22% sodium chloride solution for 45 seconds followed by 0.88 ml of 3% sodium chloride solution.

Figure 1:
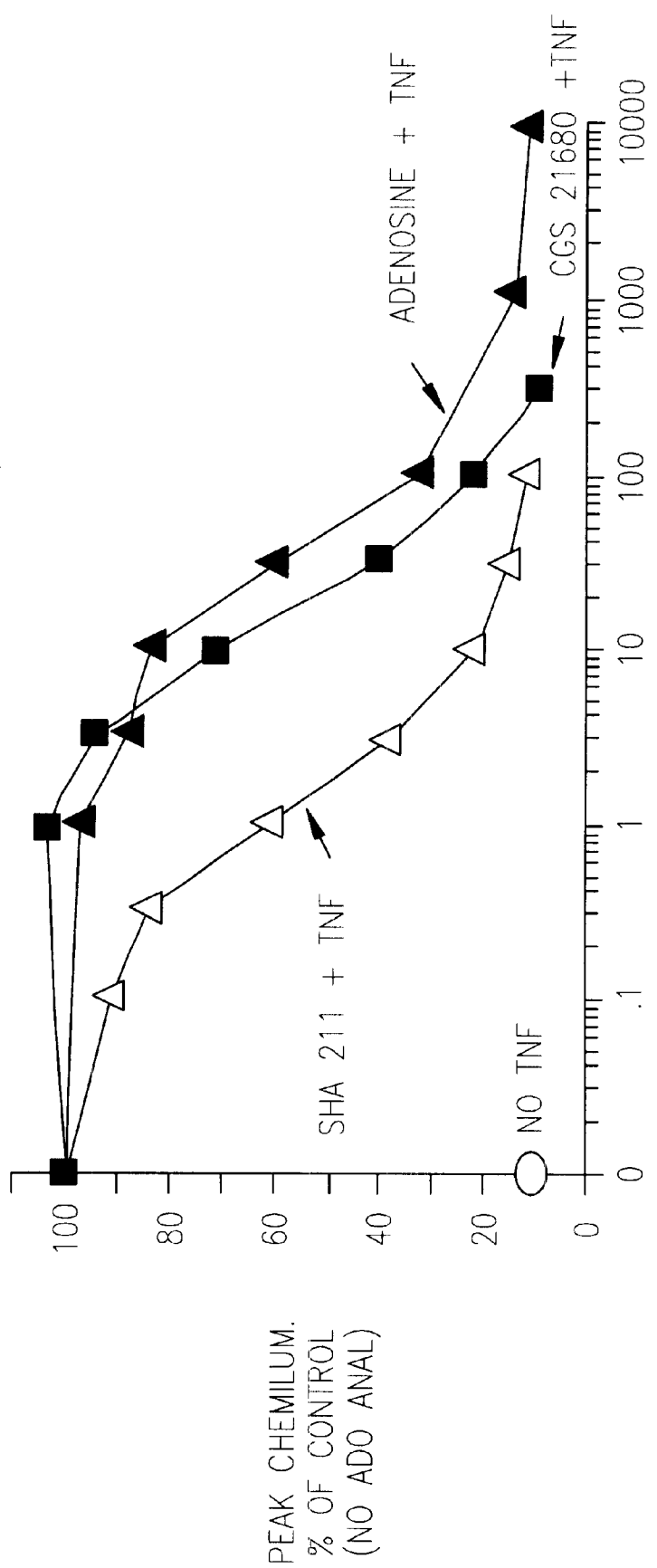
FIG. 1 illustrates the relative potencies of adenosine analogs to modulate $TNF_\alpha$-primed fMLP-stimulated polymorphonuclear cell (PMN) chemniluminescence as a measure of PMN production of oxidative products (○, no TNFα; Δ, WRC-0474[SHA 211]+TNFα; □, CGS 21680+ TNFα; and ▼, adenosine+TNFα)

Chemiluminescence: Luminol enhanced chemiluminescence, a measure of neutrophil oxidative activity, is dependent upon both superoxide production and mobilization of the granule enzyme myeloperoxidase. The light is emitted from unstable high-energy oxygen species generated by activated neutrophils. Purified PMN ($5\times10^5$/ml) were incubated in HBSS containing 0.1% human serum albumin (1 ml) with or without adenosine, adenosine analogs, and TNFα (1 U/mL) for 30 minutes at 37° C. in a shaking water bath. Then luminol ($1\times10^{-4}$M) enhanced f-met-leu-phe (1 μM) stimulated chemiluminescence was read with a Chronolog Photometer (Chrono-log Corp., Havertown, Pa.) at 37° C. for 8 min. Chemiluminescence is reported as relative peak light emitted (=height of the curve) compared to samples with TNF and without adenosine or adenosine analogs. WRC-0474[SHA 211] was 10 times more potent than either adenosine (ADO) or CGS21680 in decrease TNFα-primed f-met-leu-phe-stimulated PMN chemiluminescence (see FIG. 1).

Synergy of $A_{2A}$ Adenosine Receptor Agonist and Phosphodiesterase Inhibitors. The synergy between WRC-0474 [SHA 211] and 4-(3-cyclopentyloxy-4methoxyphenyl)-2-pyrrolidone (rolipram) was examined by measuring the effect of combined WRC-0474[SHA 211] and rolipram on TNF-primed f-met-leu-phe-stimulated suspended neutrophil superoxide release and on the oxidative burst of neutrophils adhering to matrix proteins (in this model the PMN oxidative burst is enhanced by small concentrations of TNFα [e.g. 1 U/ml] when added prior to the addition of a second stimulus such as the peptide f-met-leu-phe).

Suspended PMN Superoxide Release: Human PMN ($1\times10^6$/ml) from Ficoil-Hypaque separation were primed for 30 minutes (37° C.) with or without rhTNF (10 U/ml), with adenosine deaminase (1 U/ml), and with or without 4-(3-cyclopentyloxy4methoxyphenyl)-2-pyrrolidone and SHA 211. Cytochrome c (120 μM), catalase (0.062 mg/ml) and fMLP (100 nM) were added and the samples incubated for 10 minutes more at 37° C. SOD (200 U/ml) was added to matched samples. The samples were iced and centrifuged (2000g×10 minutes). The optical density of the supernatants were read at 550 nm against the matched SOD samples, and the umoles of SOD-inhibitable superoxide released in 10 minutes were calculated.

Figure 2:
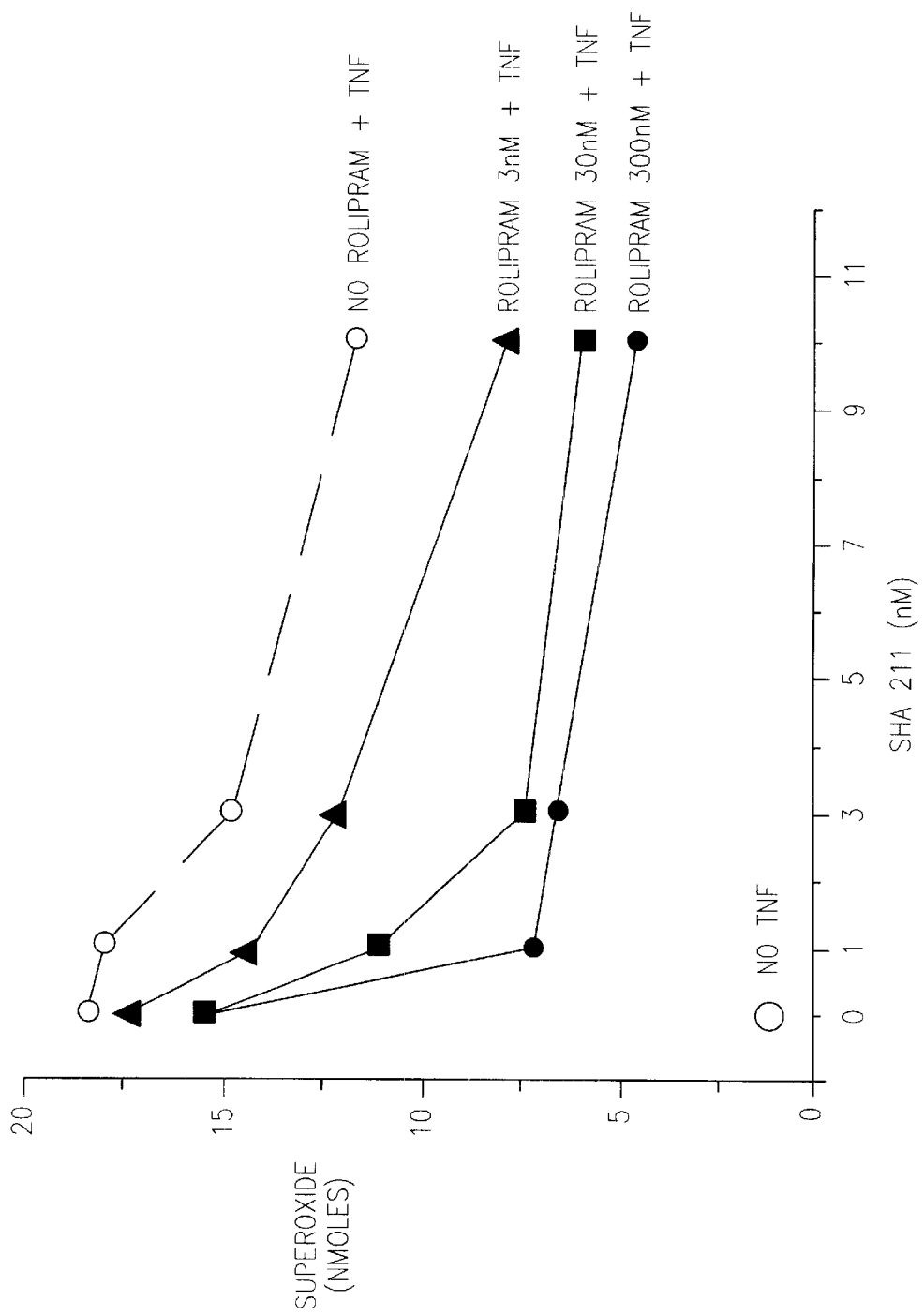
FIG. 2 illustrates the synergistic effect of WRC-0474 [SHA 211] and 4-(3-cyclopentyloxy-4-methoxyphenyl)-2-pyrrolidone (rolipram) in inhibiting TNFα-primed (10 U/ml), fMLP-stimulated (100 nM) PMN superoxide production: ○, no 4-(3-cyclopentyloxy-4-methoxyphenyl)-2-pyrrolidone; ▼, 3 nM 4-(3-cyclopentyloxy-4-methoxyphenyl)-2-pyrrolidone; □, 30 nM 4-(3- cyclopentyloxy-4-methoxyphenyl)-2-pyrrolidone; and, 300 nM 4-(3-cyclopentyloxy-4-methoxyphenyl)-2-pyrrolidone.

A synergistic effect of WRC-0474[SHA 211] and rolipram in decreasing the TNFα-primed fMLP-stimulated PMN oxidative burst was observed (see FIG. 2).

TNFα-stimulated superoxide release of PMN adherent to a matrix protein (fibrinogen) coated surface: Human PMN ($1\times10^6$/ml) from Ficoll-Hypaque separation were incubated for 90 minutes in 1 ml of Hanks balanced salt solution containing 0.1% human serum albumin, cytochrome c (120 μM), and catalase (0.062 mg/ml) in the presence and absence of rhTNF (1 U/ml), WRC-0474[SHA 211] (10 nM)

and rolipram (100 nM) in a tissue culture well which had been coated overnight with human fibrinogen. SOD (200 U/ml) was added to matched samples. The supernatants were iced and centrifuged (2000g×10 minutes) to remove any remaining suspended cells, and the optical density of the supernatants were read at 550 mn against the matched SOD samples, and the nmoles of SOD-inhibitable superoxide released in 90 minutes were calculated.

A synergistic effect of WRC-0474[SHA 211] and rolipram in decreasing the TNFα-stimulated release of superoxide from PMN adherent to fibrinogen was observed (see FIG. 3).

Effect of WRC-0474[SHA 211] with and without rolipram on TNF-Stimulated PMN Adherence to a Fibrinogen—Coated Surface. Cronstein et al., *J. Immunol.*, vol. 148, p. 2201 (1992) reported that adenosine binding to $A_1$ receptors increases PMN adherence to endothelium and matrix proteins and binding to $A_2$ receptors decreases adherence to these surfaces when the PMN are stimulated with fMLP. Despite this, others have failed to see much of an effect of adenosine (10 $\mu$M) on TNFα-stimulated PMN adherence to matrix proteins. In contrast, adenosine dramatically decreases the oxidative burst of TNFα-stimulated PMN adhering to matrix proteins (DeLa Harpe, J., *J. Immunol.*, vol. 143, p. 596 (1989)). The experiments described above establish that WRC-0474[SHA 211] decreases TNF-stimulated oxidative activity of PMN adhering to fibrinogen, especially when combined with rolipram.

PMN adherence to fibrinogen was measured as follows as adapted from Hanlon, *J. Leukocyte Biol.*, vol. 50, p. 43 (1991). Twenty-four well flat-bottomed tissue culture plates were incubated (37° C.) overnight with 0.5 ml of fibrinogen (5 mg/ml) dissolved in 1.5% $NaHCO_3$. The plates were emptied and each well washed 2× with 1 ml of normal saline. The wells were then filled with 1 ml of HBSS-0.1% human serum albumin containing PMN ($1\times10^6$/ml) with and without rhTNFα (1 U/ml), adenosine deaminase (ADA) (1 U/ML), WRC-0474[SHA 211] (10 nM), CGS21680 (30 nM), adenosine (100 nM) and rolipram (100 nM). The plates were incubated for 90 minutes at 37° C. in 5% $CO_2$. Following incubation the tissue culture wells were washed free of non-adherent cells with normal saline. The adherent monolayer of PMN was lysed with 0.1% triton-X, the amount of lactic dehydrogenase (LDH) released from the monolayer assayed (LDH kit, Sigma Co., St. Louis, Mo.), and compared to a standard curve relating the LDH content to PMN numbers. The results are shown in FIG. 4.

As a comparison to WRC-0474[SHA 211] (at only 10 nM), CGS21680 (30 nM) decreased TNF-stimulated adherence in the presence of ADA from 38% to 30% adhered (p=0.004) (see FIG. 4), and ten times as much adenosine (100 nM) decreased adherence to 28% adhered (p=0.009 compared to TNF in the presence of ADA).

Additional effects of adenosine $A_{2A}$ agonists on adherent human neutrophil oxidative activity. The bioactivity of test compounds WRC-0474[SHA 211], WRC-0470, WRC-0090 and WRC-0018 were evaluated according to the following method modified from Sullivan, G. W. et al., *Int. J. Immunonopharmacol*, 1995, 17:793–803. Neutrophils ($1\times10^6$/ml) from Ficoll-Hypaque separation were incubated for 90 minutes in 1 ml of Hanks balanced salt solution containing 0.1% human serum albumin, cytochrome c (120 $\mu$M) and catalase (0.062 mg/ml) in the presence and absence of rhTNFα (1 U/ml), WRC-0474[SHA 211], WRC-0470, WRC-0090 and WRC-0018 (3–300 nM), and rolipram (100 nM) in a tissue culture well which had been coated overnight with human fibrinogen. The supernatants were iced and centrifuged (200 g–10min) to remove any remaining suspended cells, and the optical densities of the supernatants were read at 550 nm against matched superoxide dismutase (SOD) (200 U/ml) samples. The nmoles of SOD=inhibatable superoxide released in 90 min were calculated.

FIG. 5 shows synergy between $A_{2A}$ adenosine agonists and rolipram in inhibiting TNFα-stimulated adherent PMN oxidative activity (p<0.05). WRC-0474[SHA 211] (300 nM), WRC-0470 (300 nM), WRC-0090 (300 nM) and WRC-0018 (300 nM) combined with rolipram synergistically decreased superoxide release (p<0.05). All four compounds had some activity in the presence of rolipram. WRC-0474[SHA 211] and WRC-0470 were the most active. Nanomolar concentrations of WRC0474[SHA 211] resulted in biphasic activity. All compounds were synergistic with rolipram to decrease TNFα-stimulated adherent PMN oxidative activity.

PMN degranulation (adherent cells) The following methods were adapted from Sullivan, G. W. and G. L. Mandell, *Infect. Inumun.*, 1980: 30:272–280. Neutrophils ($3.1\times10^6$/ml) from Ficoll-Hypaque separation were incubated for 120 minutes in 1 ml of Hanks balanced salt solution containing 0.1% human serum albumin, ±rh TNFα (10 U/ml), ±WRC-0470 (3–300 nM), and ±rolipram (300 nM) in a tissue culture well which had been coated overnight with human fibrinogen. The supernatant fluids with any suspended neutrophils were harvested following incubation, centrifuged (2000×g for 10 min) to remove any suspended cells and the cell-free supernatants frozen. Release of lysozyme, a component of neutrophil primary and secondary granules was assayed. Lysis of a suspension of *Micrococcus lysodeikticus* by the "cell-free supernatant" was measured by spectrophotometric analysis (540 mm) to determine the amount of release of granule contents to the surrounding medium.

Results showed that WRC-0470 (300 nM) with rolipram (300 nM) significantly decreased TNFα-stimulated adherent neutrophil degranulation 67%; P=0.027. The data indicate that in addition to decreasing TNFα-stimulated PMN adherent and the oxidative burst of these adherent neutrophils; WRC-0470 also decreases degranulation activated PMN adhering to a biological surface.

PMN oxidative. activity in whole blood The following methods were adapted from Rothe, G. A. et al., *J. Immunol. Meth.* 1991; 138:133–135). Heparinized whole blood (0.8 ml) was incubated (37°; 30 min) with adenosine deaminase (ADA, 1 U/ml), catalase (14,000 U/ml), ±dihydrorhodamine 123, ±WRC-0470 (3–300 nM), ±rolipram (300 nM) and ±TNFα (10 U/ml). The primed blood samples were stimulated with fMLP (15min), then iced, the red blood cells lysed with FACS lysing solution (3ecton-Dickinson, San Jose, Calif.), washed and the leukocytes resuspended in phosphate buffered saline (PBS) These samples containing mixed leukocytes were gated for neutrophils by forward and side scatter and the fluorescence of 10,000 neutrophils measured in the FL1 channel of a FACScan (Beckton-Dickinson) fluorescence activated cell sorter.

The results are reported as relative mean florescence intensity in FIG. 6 of the drawings. WRC0470 decreased oxidative activity of TNFα-primed fMLP-stimulated neutrophils in whole blood and acted synergistically with rolipram. WRC0470 (30–300 nM) decreased neutrophil oxidative activity synergistically with rolipram (300 nM) in samples stimulated with fMLP and in blood samples primed with TNFα and then stimulated with fMLP.

Production of TNFα by purified human adherent monocytes A monocyte rich monolayer (>95% monocytes) was prepared by incubating 1 ml of the mononuclear leukocyte fraction ($5\times10^5$/ml) from a Ficoll-Hypaque separation in wells of a 24 well tissue culture plate (1 hr; 37° C.; 5% $CO_2$). The non-adherent leukocytes were removed by washing and culture medium added to the wells (1 ml RPMI 1640 containing 1.5 mM HEPES-1% autologous serum with penicillin and streptomycin (250 U/ml and 250 μg/ml, respectively) and ADA (1 U/ml) ±WRC-0470 (30–100 nM), ±endotoxin (10 ng/ml), ±rolipram (300 nM) and ±the adenosine $A_{2A}$ selective antagonist 4-(2-[7-amino-2-(2-furyl)[1,2,4]-triazolo[2,3a-[1,3,5]trazinyl-amino]ethyl)-phenol (ZM241385) (50 nM). The samples were incubated for 4 hr (37° C.; 5% $CO_2$) and the supernatants harvested. Any suspended cells were removed by centrifugation and the cell-free samples frozen (−70° C.). TNFα was assayed in the cell-free supernatants by an ELISA kit (Cistron Biotechnology, Pine Brook, N.J.).

As shown in FIGS. 7A and 7B, WRC-0470 ±rolipram decreased endotoxin-stimulated adherent monocyte production of TNFα ($P<0.050$). As illustrated in FIG. 7B, the $A_{2A}$ selective antagonist ZM241385 significantly inhibited the effect of WRC-0470 (300 nM) combined with rolipram (300 nM ($p=0.020$) on TNFα release from monocytes. Hence, WRC-0470 affects TNFα-stimulated neutrophil activity and decreases endotoxin-stimulated TNFα production by monocytes.

Effects of WRC-0470 and rolipram on the extravasation of white blood cells in a rat model of inflammation Adult wistar rats (approximately 200 g) were anesthetized with intermuscular injections of ketamine and xylazine. Bacteria meningitis (BM) was induced via intracisternal inoculation of either *E. coli* strain 026: B6LPS (200 ng), cytokines (IL-1 and TNFα, or LPS plus cytokines). The animals were then infused with rolipram and/or WRC-1470 over the duration of the experiment using a Harvard pump. CSF (cerebrospinal fluid) and blood was then sampled at 4 h postinoculation and alterations in BBBP (blood-brain barrier permeability) and WBC (white blood cell) counts were determined. CSF and WBC concentrations were determined with standard hemacytometer methods. For assessment of % BBBP, rats were given an intravenous injection of 5 μCi 125I-labeled bovine serum albumin concomitant with intracisternal inoculation. Equal samples of CSF and blood were read simultaneously in a gamma counter and after subtraction of background radioactivity, % BBBP was calculated by the following formula: % BBBP=(cpm CSF/cpm blood)× 100. All statistical tests were performed using Instat biostatistical software to compare the post-inoculation samples of experimental rats with the control rats. The statistical tests used to generate p-values were Student's t-test and ANOVA.

Results of the tests are reported in FIGS. 8 and 9. Infusion of WRC-0470 at a rate of 0.005–1.2μg/kg/hr inhibited pleiocytosis ($p>0.05$ as compared to control). The effect of WRC-0470 on BBBP is shown in FIG. 9. A significant response is seen with a range of 0.01–0.015 μg/kg/hr ($p<0.05$ as compared to control). A rebound effect is noted with the administration of 1.2 μg/kg/hr where %BBBP returned to control. FIG. 10 shows the effect of rolipram on CSF pleocytosis in a range of 0–0.01 μg/kg/hr with 0.01 μg/kg/hr inhibiting 99% of the pleocytosis ($p<0.05$). Rolipram at either 0.01 or 0.005 μg/kg/hr showed significant inhibition of alterations of BBBP ($p>0.05$), while a dose of 0.002 μg/kg/hr had no significant effect The effect of a combination of rolipram and WRC-0470 on CSF WBC pleocytosis is illustrated in FIG. 11. Rolipram (0.001 μg/kg/hr) in combination with WRC-0470 (0.1 μg/kg/hr) inhibited migration of WBC's (200±70WBC/μl) into the sub-arachnoid space (SAS) to a greater extent than did either rolipram (1,670±1,273WBC/μl, $p<0.050$) or WRC-0470 (600±308WBCs/μl, $p<0.050$) alone. The data show a powerful inhibiting effect of WRC-0470 and a synergy with rolipram to prevent inflammation in an animal model.

Application of $A_{2A}$ adenosine receptors with or without rolipram on balloon angioplasty and gene therapy. Balloon angioplasty is commonly used to treat coronary artery stenosis. Restenosis following balloon angioplasty (BA) occurs in up to 40% of coronary interventions. Holmes et al., *American Journal of Cardiology*, 53: 77C–81C (1984). (40%). Restenosis results from a complex interaction of biologic processes, including (i) formation of platelet-rich thrombus; (ii) release of vasoactive and mitogenic factors causing migration and proliferation of smooth muscle cells (SMC); (iii) macrophage and other inflammatory cell accumulation and foam cell (FC) formation; (iv) production of extracellular matrix; and (v) geometric remodeling. Recently the use of coronary stents and pharmacologic intervention using a chimeric antibody to block the integrin on platelets have been partially successful in limiting restenosis after percutaneous coronary interventions in man. Topol et al., *Lencet*, 343: 881–886 (1994). Since inflammatory cell infiltration might be central to the response to injury, and restenotic processes, and adenosine, active via $A_{2A}$ adenosine receptors, inhibits tissues inflammatory cell accumulation, we hypothesize that agonists of $A_{2A}$ adenosine receptors ±type IV PDE inhibitors will reduce the incidence of restenosis following balloon angioplasty.

In addition, recent advances in local delivery catheters and gene delivery techniques raise the interesting and exciting possibility of administering genes locally into the vessel wall. Nabel et al., *Science*, 249: 1285–1288 (1990); Leclerc et al., *Journal of Clinical Investigation*, 90: 936–944 (1992). Adenoviral-mediated gene transfer affords several advantages over other techniques. However, gene expression is only transient, and has been observed for 7–14 days with diminuition or loss of expression by 28 days. Lack of persistence may result from host immune cytolytic responses directed against infected cells. The inflammatory response generated by the present generation of adenovirus results in neoitimal lesion formation and may thus offset the benefit of a therapeutic gene. Newman et al., *Journal of Clinical Investigation*, 96: 2955–2965 (1995). An $A_{2A}$ adenosine receptor agonist ±a type IV phosphodiesterase inhibitor in combination with adenovirus may improve the efficiency of gene transfer.

Obviously, numerous modifications and variations of the present invention are possible in light of the above teachings. It is therefore to be understood that, within the scope of the appended claims, the invention may be practiced otherwise than as specifically described herein.

What is claimed is:

1. A method for reducing or preventing restenosis, during or following balloon angioplasty, comprising administering to a mammal in need thereof an effective anti-inflammatory amount of agonist of an $A_{2A}$ adenosine receptor in combination with an effective amount of a Type IV phosphodiesterase inhibitor.

2. The method of claim 1, wherein said agonist of an $A_{2A}$ adenosine receptor has the formula (I)

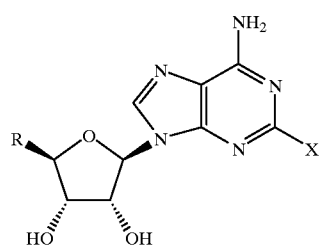

(I)

wherein X is a group selected from the group consisting of —OR$^1$, —NR$^2$R$^3$, and —NH—N=R$^4$;

wherein R¹ is $C_{1-4}$-alkyl; $C_{1-4}$-alkyl substituted with one or more $C_{1-4}$-alkoxy groups, halogens, hydroxy groups, amino groups, mono($C_{1-4}$-alkyl)amino groups, di($C_{1-4}$-alkyl)amino groups, or $C_{6-10}$-aryl groups, wherein the aryl groups may be substituted with one or more halogens, $C_{1-4}$-alkyl groups, hydroxy groups, amino groups, mono($C_{1-4}$-alkyl)amino groups, or di($C_{1-4}$-alkyl)amino groups; $C_{6-10}$-aryl; or $C_{6-10}$-aryl substituted with one or more halogens, hydroxy groups, amino groups, mono($C_{1-4}$-alkyl)amino groups, di($C_{1-4}$-alkyl)amino groups, or $C_{1-4}$-alkyl groups;

one of R² and R³ has the same meaning as R¹ and the other is hydrogen; R⁴ is a group having the formula:

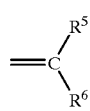

(II)

wherein each of R⁵ and R⁶ independently may be hydrogen, $C_{3-7}$-cycloalkyl, or any of the meanings of R¹, provided that R⁵ and R⁶ are not both hydrogen; and R is —CH₂OH, —CH₃, —CO₂R⁷, or —C(=O)NR⁸R⁹; wherein R⁷ has the same meaning as R¹ and wherein R⁸ and R⁹ have the same meaning as R⁵ and R⁶, and R⁸ and R⁹ may both be hydrogen;

or a pharmaceutically acceptable salt thereof.

3. The method of claim 2, wherein the agonist of an $A_{2A}$ adenosine receptor is administered following balloon angioplasty.

4. The method of claim 2, wherein the agonist of an $A_{2A}$ adenosine receptor is administered during balloon angioplasty.

5. The method of claims 2, wherein said agonist of an $A_{2A}$ adenosine receptor is selected from the group consisting of:

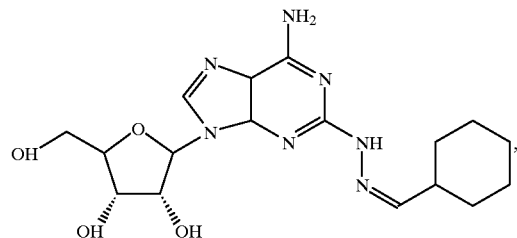

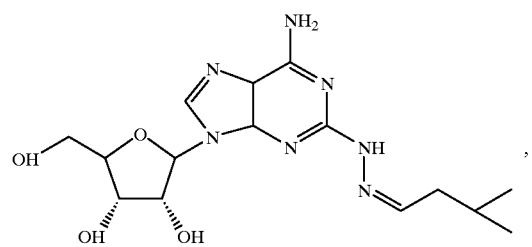

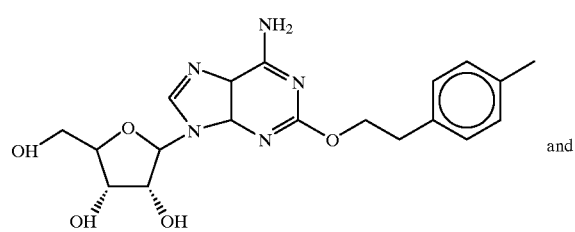

and

-continued

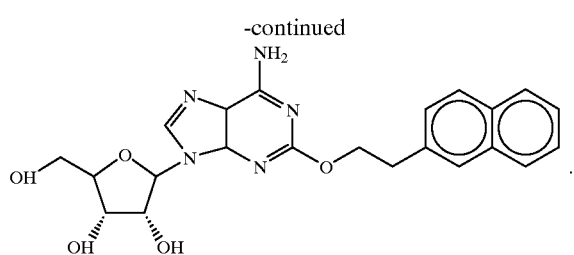

6. The method of claim 1, wherein said Type IV phosphodiesterase inhibitor is a compound having formula (V):

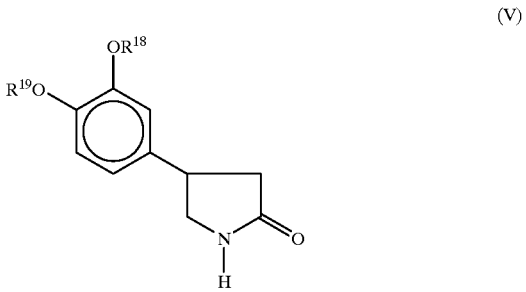

(V)

wherein R¹⁸ and R¹⁹ each are alike or different and are hydrocarbon radicals having up to 18 carbon atoms with at least one being other than methyl, a heterocyclic ring, or alkyl of 1–5 carbon atoms which is substituted by one or more of halogen atoms, hydroxy, carboxy, alkoxy, alkoxycarbonyl or an amino group; or amino.

7. The method of claim 1, wherein said type IV phosphodiesterase inhibitor is rolipram.

8. The method of claim 1, wherein said agonist of an $A_{2A}$ adenosine receptor is

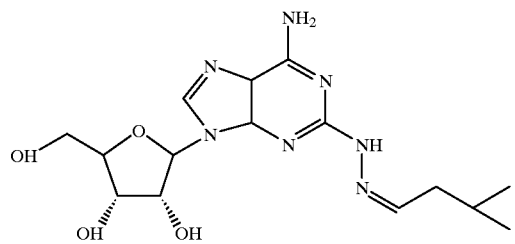

and said Type IV phosphosterase inhibitor is rolipram.

9. The method of claim 1, wherein said agonist of an $A_{2A}$ adenosine receptor is

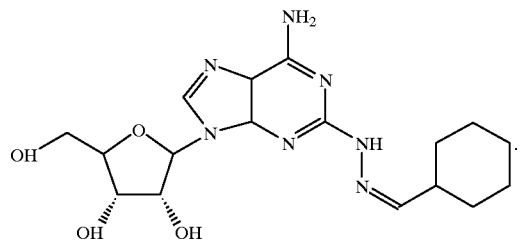

and said Type IV phosphosterase inhibitor is rolipram.

10. The method of claim 3, wherein said $A_{2A}$ adenosine receptor agonist and said T Type IV phosphosterase inhibitor are co-administered together to the mammal in need thereof.

\* \* \* \* \*